US011759447B1

(12) United States Patent
Raskin

(10) Patent No.: US 11,759,447 B1
(45) Date of Patent: *Sep. 19, 2023

(54) COMPOUND AND METHOD FOR TREATING DISEASES AND DISORDERS

(71) Applicant: RCR BIOPHARMA, Los Angeles, CA (US)

(72) Inventor: Irena Raskin, Pacific Palisades, CA (US)

(73) Assignee: RCR Biopharma, Los Angeles, CA (US)

( * ) Notice: Subject to any disclaimer, the term of this patent is extended or adjusted under 35 U.S.C. 154(b) by 285 days.

This patent is subject to a terminal disclaimer.

(21) Appl. No.: 16/913,878

(22) Filed: Jun. 26, 2020

Related U.S. Application Data

(60) Provisional application No. 62/867,116, filed on Jun. 26, 2019.

(51) Int. Cl.
| *A61K 31/352* | (2006.01) |
| *A61K 9/08* | (2006.01) |
| *A61K 31/05* | (2006.01) |
| *A61K 47/14* | (2017.01) |

(52) U.S. Cl.
CPC ........... *A61K 31/352* (2013.01); *A61K 9/08* (2013.01); *A61K 31/05* (2013.01); *A61K 47/14* (2013.01); *A61K 2236/33* (2013.01); *A61K 2236/35* (2013.01)

(58) Field of Classification Search
None
See application file for complete search history.

(56) References Cited

U.S. PATENT DOCUMENTS

| 9,095,555 | B2 | 6/2014 | Winnicki | |
| 2004/0033280 | A1* | 2/2004 | Whittle et al. | ....... A61K 31/352 |
| | | | | 549/392 |
| 2016/0279073 | A1* | 9/2016 | Donsky et al. | ...... A61K 31/045 |

(Continued)

FOREIGN PATENT DOCUMENTS

| CA | 2974895 A1 | 7/2016 |
| CA | 2988435 A1 | 6/2018 |
| CA | 3046320 A1 | 6/2018 |
| CA | 3020140 A1 | 4/2019 |

(Continued)

OTHER PUBLICATIONS

Alexa Peters, Treating Your Dog With Cbd, Healthline Media a Red Ventures Company.
Ashley Sobel, What is Limonnene? Everything you Need to Know, Healthline, May 22, 2019.

(Continued)

*Primary Examiner* — Kyung S Chang
(74) *Attorney, Agent, or Firm* — RISSO I.P.

(57) ABSTRACT

Described is a cannabinoid-terpenoid solution (CTS) and method of treating a disease state or condition in animals other than humans via cannabinoid-terpenoid therapy. The CTS includes a unique combination of cannabinoids, terpenoids (terpenes), and a lipophilic carrier to allow safely and effectively treat the animal.

31 Claims, 19 Drawing Sheets

600 / 602

| 1:1 | | | Actual | | | | Range | | |
|---|---|---|---|---|---|---|---|---|---|
| Ingredient | | Total (mg) | % of CATEGORY (Either Cannabinoid or Terpenoid) | % of ACTIVE Ingredients (Cannabinoid AND Terpenoid) | % of TOTAL (Active & Inactive mg per 1 mL) Ingredients | UNIT OF MEASURE (mg PER 1 mL) | % of CATEGORY (Either Cannabinoid or Terpenoid | % of ACTIVE Ingredients (Cannabinoid AND Terpenoid) | % of TOTAL (Active & Inactive mg per 1 mL) Ingredients |
| Cannabinoids | Total | 4 | 100% | 20% | 5% | | | ≥ 15% to ≤ 40% | ≥ 2% to ≤ 10% |
| CBD | | 2 | 50% | 10% | 3% | | ≥ 25% to ≤ | ≥ 7.5% to ≤ 10% | ≥ 1% to ≤ 5% |
| THC | | 2 | 50% | 10% | 3% | | ≥ 50% to ≤ | ≥ 7.5% to ≤ 30% | ≥ 1% to ≤ 5% |
| THCV | | | | | | | | | |
| CBDV | | | | | | | | | |
| CBN | | | | | | | | | |
| CBG | | | | | | | | | |
| CBDA | | | | | | | | | |
| THCA | | | | | | | | | |
| Terpenoids | Total | 16 | 100% | 80% | 20% | | | ≥ 60% to ≤ 85% | ≥ 10% to ≤ 30% |
| B-Caryophyllene | | | | ← | | | | ≥ 7% to ≤ 30% | ≥ 0.5% to ≤ 8% |
| Linalool | | | | ← | | | | ≥ 7% to ≤ 30% | ≥ 0.5% to ≤ 8% |
| D-Limonene | | | | ← | | | | ≥ 7% to ≤ 30% | ≥ 0.5% to ≤ 8% |
| B-Mycene | | | | ← | | | | ≥ 7% to ≤ 30% | ≥ 0.5% to ≤ 8% |
| A-Pinene | | | | ← | | | | ≥ 7% to ≤ 30% | ≥ 0.5% to ≤ 8% |
| Humulene | | | | ← | | | | ≥ 6% to ≤ 70% | ≥ 2% to ≤ 25% |
| Guanine | | | | | | | | ≥ 7% to ≤ 30% | ≥ 0.5% to ≤ 8% |
| Active Ingredients | Total | 20 | | 100% | 25% | | | | ≥ 15% to ≤ 30% |
| Excipient Inactive | Total | 80 | | | 75% | | | | ≥ 70% to ≤ 85% |

(56) References Cited

U.S. PATENT DOCUMENTS

| | | | |
|---|---|---|---|
| 2018/0193399 | A1 | 7/2018 | Kariman |
| 2018/0228788 | A1 | 8/2018 | Mukunda et al. |
| 2018/0243259 | A1* | 8/2018 | Nguyen ............... A61K 36/185 |
| 2018/0271924 | A1 | 9/2018 | Kariman |
| 2018/0344684 | A1* | 12/2018 | Vu et al. ................. A61K 9/007 |
| 2019/0080826 | A1 | 3/2019 | Kamensek et al. |
| 2019/0201463 | A1 | 7/2019 | Kariman |
| 2020/0030282 | A1 | 1/2020 | Koltai et al. |
| 2020/0046722 | A1 | 2/2020 | Mukunda |
| 2020/0101041 | A1 | 4/2020 | Kleidon |
| 2020/0179342 | A1 | 6/2020 | Mukunda et al. |

FOREIGN PATENT DOCUMENTS

| | | |
|---|---|---|
| CN | 108135869 A | 6/2018 |
| CN | 109069475 A | 12/2018 |
| CN | 110121337 A | 8/2019 |
| CN | 110382007 A | 10/2019 |
| KR | 20190124785 A | 11/2019 |
| WO | 2016094810 A2 | 6/2016 |
| WO | 2017218853 A1 | 12/2017 |
| WO | 2019071213 A1 | 4/2019 |
| WO | 2019077611 A1 | 4/2019 |
| WO | 2019190608 A1 | 10/2019 |
| WO | 2019198056 A1 | 10/2019 |
| WO | 2019237156 A1 | 12/2019 |

OTHER PUBLICATIONS

CannaCompanion, Ultimate Guide to Cannabis for Dogs and Cats, Cannacompanion, Oct. 25, 2017.
Gary Ritchter, Cbd & Cannabis for Pets in Pain, Project Cbd, May 1, 2019.
Li et al., Vegetable Oils as Alternative Solvents for Green Oleo-extraction, Purification and Formulation of Food and Natural Products, Molecules, Sep. 5, 2017.
Non-Final Rejection, U.S. Appl. No. 16/913,834, dated May 12, 2022.
Notice of Allowance, U.S. Appl. No. 16/913,834, dated Dec. 22, 2022.
Product Monograph Including Patient Medication Information, Apr. 15, 2005.
Stephen Cital, Cannabis for Animals: A Look Into Cannabis as Medicine for Pets, Apr. 5, 2019, Australia.
The Animal Keeper, Cbd Oil and Your Pet's Health, Mar. 3, 2020.
TheSourceENV, Intro to Terpenes, TheSourcenv, Jun. 5, 2018.

* cited by examiner

| Cannabinoid-Terpenoid Compound Solution Active Ingredients | | |
|---|---|---|
| Cannabinoids | Pharmacological Activity (Ref.) | Synergistic Terpenoid |
| CBD | AI/antioxidant (Hampson et al., 1998) | Limonene et al. |
| | Anti-anxiety via 5-HT1A(Russo et al., 2005) | Linalool, limonene |
| | Anticonvulsant (Jones et al., 2010) | Linalool |
| | Cytotoxic versus breast cancer (Ligresti et al., 2006) | Limonene |
| | Effective versus MRSA (Appendino et al., 2008) | Pinene |
| THC | Analgesic via CB1 and CB2 (Rahn and Hohmann, 2009) | Various |
| | AI/antioxidant (Hampson et al., 1998) | Limonene et al. |
| | Bronchodilatory (Williams et al., 1976) | Pinene |
| | Benefit on duodenal ulcers (Douthwaite, 1947) | Caryophyllene, limonene |
| | Muscle relaxent (Kavia et al., 2010) | Linalool? |
| | Antipruritic, cholestatic jaundice (Neff et al., 2002) | Caryophyllene? |
| THCV (Tetrahydrocannabivarin) | Anticonvulsant (Hill et al., 2010) | Linalool |
| CBDV (Cannabidivarin) | Anticonvulsant in hippocampus (Hill et al., 2010) | Linalool |
| CBG (Cannabigerol) | TRPM8 antagonist prostate cancer (De Petrocellis et al., 2011) | Cannabis terpenoids |
| | GABA uptake inhibitor (Banerjee et al., 1975) | Phytol, linalool |
| | Anti-fungal (ElSohly et al., 1982) | Caryophyllene oxide |
| | Antidepressant (Musty and Deyo, 2006); via 5-HT1A antagonism (Cascio et al., 2010) | Limonene |
| | Effective versus MRSA (Appendino et al., 2008) | Pinene |
| | AI/anti-hyperalgesic (Bolognini et al., 2010) | Caryophyllene et al.... |
| Terpenoids | Pharmacological Activity (Ref.) | Synergistic Cannabinoid |
| α-pinene | Anti-inflammatory va PGE-1 (GIL et al., 1989) | CBD |
| | Bronchodilatory in humans (Falk et al., 1990) | THC, CBD |
| | Acetylcholinesterase inhibitor, aiding memory (Perry et al., 2000) | THC, CBD |
| β-myrcene | Blocks inflammation via PGE-2 (Lorenzetti et al., 1991) | CBD |
| | Analgesic, antagonized by naloxone (Rao et al., 1990) | CBD, THC |
| | Sedating, muscle relaxant, hypnotic (do Vale et al., 2002) | THC |
| | Blocks hepatic carcinogenisis by aflatoxin (de Oliveira et al, 1997) | CBD, CBG |
| D-limonene | Potent AD/immunostimulant via inhalation (Komori et al. 1995) | CBD |
| | Anxiolytic (Carvalho-Freitas and Costa, 2002; Pultrini Ade et al., 2006) | CBD |
| | Apoptosis of breast cancer cells (Vigushin et al., 1998) | CBD, CBG |
| | Active against acne bacteria (Kim et al., 2008) | CBD |
| | Dermatophytes (Sanguinetti et al., 2007; Singh et al., 2010) | CBG |
| | Gastro-oesophageal reflux (Harris, 2010) | THC |
| Linalool | Anti-anxiety (Russo, 2001) | CBD, CBG |
| | Sedative on inhalation in mice (Buchbauer et al., 1993) | THC |
| | Local anesthetic (Re et al., 2000) | THC |
| | Anal gesic via adenosine A2A (Peana et al., 2006) | CBD |
| | Anticconvulsant/anti-glutamate (Elisabetsky et al., 1995) | CBD, THCV, CBDV |
| β-caryophyllene | AI via PGE-1 comparable phenylbutazone (Basile et al., 1988) | CBD |
| | Gastric cytoprotective (Tambe et al., 1996) | THC |
| | Selective CB2 agonist (100 nM) (Gertsch et al., 2008) | THC |
| | Treatment of pruritus? (Karsak et al., 2007) | THC |
| | Treatment of addiction? (Xi et al., 2010) | CBD |

FIG. 1

| Formulation | CBD:THC | Sample Conditions Treated | Terpenoids | Unexpected Results |
|---|---|---|---|---|
| CBD Dominant | 20:1 | Anxiety | Terpenoids are majority of active ingredients | Surprisingly, calms without sedation or change in behavior other than calming effect |
| CBD Rich | 4:1 | Seizures | Terpenoids are majority of active ingredients | Surprisingly, ends seizures |
| CBD Balanced with THC | 1:1 | Inflammatory Bowel Disease | Fewer overall cannabinoids per dose | Surprisingly, as THC increases, fewer overall cannabinoids are required for effective treatment |
| THC Rich | 1:4 | Severe Pain from Arthritis or Cancer | Fewer overall cannabinoids per dose | Surprisingly, treats pain without sedation or other negative effects |
| THC Dominant | 1:20 | Appetite Stimulation | Fewer overall cannabinoids per dose | Surprisingly, stimulates appetite while lower doses of THC do not seem to increase or stimulate appetite |

| Ingredient | | Actual | | | | Range | | | |
|---|---|---|---|---|---|---|---|---|---|
| | | UNIT OF MEASURE (mg PER 1 mL) | % of CATEGORY (Either Cannabinoid or Terpenoid) | % of ACTIVE Ingredients (Cannabinoid AND Terpenoid) | % of TOTAL (Active & Inactive mg per 1 mL) Ingredients | UNIT OF MEASURE (mg PER 1 mL) | % of CATEGORY (Either Cannabinoid or Terpenoid) | % of ACTIVE Ingredients (Cannabinoid AND Terpenoid) | % of TOTAL (Active & Inactive mg per 1 mL) Ingredients |
| Cannabinoids | Total | 10 | | 45% | 13% | | | ≥ 30% to ≤ 60% | ≥ 9% to ≤ 25% |
| CBD | | 9.5 | 95% | 43% | 12% | | ≥ 80% to ≤ | ≥ 30% to ≤ 55% | ≥ 7% to ≤ 15% |
| THC | | 0.5 | 5% | 2% | 1% | | ≥ 0.4% to ≤ | ≥ 1% to ≤ 10% | ≥ 1% to ≤ 10% |
| THCV | | | | | | | | | |
| CBDV | | | | | | | | | |
| CBN | | | | | | | | | |
| CBG | | | | | | | | | |
| CBDA | | | | | | | | | |
| THCA | | | | | | | | | |
| Terpenoids | Total | 12 | | 55% | 15% | | | ≥ 40% to ≤ 70% | ≥ 5% to ≤ 25% |
| B-Caryophyllene | | | | | | | | ≥ 6% to ≤ 70% | ≥ 2% to ≤ 25% |
| Linalool | | | | | | | | ≥ 6% to ≤ 70% | ≥ 2% to ≤ 25% |
| D-Limonene | | | | | | | | ≥ 6% to ≤ 70% | ≥ 2% to ≤ 25% |
| B-Mycene | | | | | | | | ≥ 6% to ≤ 70% | ≥ 2% to ≤ 25% |
| A-Pinene | | | | | | | | ≥ 6% to ≤ 70% | ≥ 2% to ≤ 25% |
| Humulene | | | | | | | | ≥ 6% to ≤ 70% | ≥ 2% to ≤ 25% |
| Guanine | | | | | | | | ≥ 6% to ≤ 70% | ≥ 2% to ≤ 25% |
| Active Ingredients | Total | 22 | | 100% | 28% | | | | ≥ 15% to ≤ 30% |
| Excipient Inactive | Total | 78 | | | 72% | | | | ≥ 70% to ≤ 85% |

400 — Actual; 402 — Range

| Ingredient | | Total (mg) | Actual | | | Range | | | |
|---|---|---|---|---|---|---|---|---|---|
| | | | % of CATEGORY (Either Cannabinoid or Terpenoid) | % of ACTIVE Ingredients (Cannabinoid AND Terpenoid) | % of TOTAL (Active & Inactive mg per 1 mL) Ingredients | UNIT OF MEASURE (mg PER 1 mL) | % of CATEGORY (Either Cannabinoid or Terpenoid) | % of ACTIVE Ingredients (Cannabinoid AND Terpenoid) | % of TOTAL (Active & Inactive mg per 1 mL) Ingredients |
| Cannabinoids | Total | 10 | | 42% | 13% | | | ≥ 35% to ≤ 70% | ≥ 9% to ≤ 40% |
| CBD | | 8 | 80% | 33% | 11% | | ≥ 50% to ≤ | ≥ 30% to ≤ 40% | ≥ 7% to ≤ 30% |
| THC | | 2 | 20% | 8% | 3% | | ≥ 18% to ≤ | ≥ 5% to ≤ 10% | ≥ 2% to ≤ 10% |
| THCV | | | | | | | | | |
| CBDV | | | | | | | | | |
| CBN | | | | | | | | | |
| CBG | | | | | | | | | |
| CBDA | | | | | | | | | |
| THCA | | | | | | | | | |
| Terpenoids | Total | 14 | 100% | 58% | 18% | | | ≥ 30% to ≤ 65% | ≥ 15% to ≤ 60% |
| B-Caryophyllene | | | | | | | | ≥ 6% to ≤ 65% | ≥ 1% to ≤ 25% |
| Linalool | | | | | | | | ≥ 6% to ≤ 65% | ≥ 1% to ≤ 25% |
| D-Limonene | | | | | | | | ≥ 6% to ≤ 65% | ≥ 1% to ≤ 25% |
| B-Mycene | | | | | | | | ≥ 6% to ≤ 65% | ≥ 1% to ≤ 25% |
| A-Pinene | | | | | | | | ≥ 6% to ≤ 65% | ≥ 1% to ≤ 25% |
| Humulene | | | | | | | | ≥ 6% to ≤ 70% | ≥ 2% to ≤ 25% |
| Guanine | | | | | | | | ≥ 6% to ≤ 65% | ≥ 1% to ≤ 25% |
| Active Ingredients | Total | 24 | | 100% | 32% | | | | ≥ 27% to ≤ 40% |
| Excipient Inactive | Total | 76 | | | 68% | | | | ≥ 60% to ≤ 73% |

500 — Actual; 502 — Range

FIG. 5

| 1:1 | | | Actual | | | | | Range | | |
|---|---|---|---|---|---|---|---|---|---|---|
| Ingredient | | Total (mg) | % of CATEGORY (Either Cannabinoid or Terpenoid) | % of ACTIVE Ingredients (Cannabinoid AND Terpenoid) | % of TOTAL (Active & Inactive mg per 1 mL) Ingredients | UNIT OF MEASURE (mg PER 1 mL) | % of CATEGORY (Either Cannabinoid or Terpenoid) | % of ACTIVE Ingredients (Cannabinoid AND Terpenoid) | % of TOTAL (Active & Inactive mg per 1 mL) Ingredients |
| Cannabinoids | Total | 4 | 100% | 20% | 5% | | | ≥ 15% to ≤ 40% | ≥ 2% to ≤ 10% |
| CBD | | 2 | 50% | 10% | 3% | | ≥ 25% to ≤ | ≥ 7.5% to ≤ 10% | ≥ 1% to ≤ 5% |
| THC | | 2 | 50% | 10% | 3% | | ≥ 50% to ≤ | ≥ 7.5% to ≤ 30% | ≥ 1% to ≤ 5% |
| THCV | | | | | | | | | |
| CBDV | | | | | | | | | |
| CBN | | | | | | | | | |
| CBG | | | | | | | | | |
| CBDA | | | | | | | | | |
| THCA | | | | | | | | | |
| Terpenoids | Total | 16 | 100% | 80% | 20% | | | ≥ 60% to ≤ 85% | ≥ 10% to ≤ 30% |
| B-Caryophyllene | | | | | | | | ≥ 7% to ≤ 30% | ≥ 0.5% to ≤ 8% |
| Linalool | | | | | | | | ≥ 7% to ≤ 30% | ≥ 0.5% to ≤ 8% |
| D-Limonene | | | | | | | | ≥ 7% to ≤ 30% | ≥ 0.5% to ≤ 8% |
| B-Mycene | | | | | | | | ≥ 7% to ≤ 30% | ≥ 0.5% to ≤ 8% |
| A-Pinene | | | | | | | | ≥ 7% to ≤ 30% | ≥ 0.5% to ≤ 8% |
| Humulene | | | | | | | | ≥ 6% to ≤ 70% | ≥ 2% to ≤ 25% |
| Guanine | | | | | | | | ≥ 7% to ≤ 30% | ≥ 0.5% to ≤ 8% |
| Active Ingredients | Total | 20 | | 100% | 25% | | | | ≥ 15% to ≤ 30% |
| Excipient Inactive | Total | 80 | | | 75% | | | | ≥ 70% to ≤ 85% |

| Ingredient | | Total (mg) | Actual | | | | Range | | | |
|---|---|---|---|---|---|---|---|---|---|---|
| | | | % of CATEGORY (Either Cannabinoid or Terpenoid) | % of ACTIVE Ingredients (Cannabinoid AND Terpenoid) | % of TOTAL (Active & Inactive mg per 1 mL) Ingredients | UNIT OF MEASURE (mg PER 1 mL) | % of CATEGORY (Either Cannabinoid or Terpenoid) | % of ACTIVE Ingredients (Cannabinoid AND Terpenoid) | % of TOTAL (Active & Inactive mg per 1 mL) Ingredients |
| Cannabinoids | Total | 10 | 100% | 42% | 13% | | | ≥ 35% to ≤ 70% | ≥ 9% to ≤ 40% |
| CBD | | 2 | 20% | 8% | 3% | | ≥ 18% to ≤ | ≥ 5% to ≤ 10% | ≥ 2% to ≤ 10% |
| THC | | 8 | 80% | 33% | 11% | | ≥ 50% to ≤ | ≥ 30% to ≤ 40% | ≥ 7% to ≤ 30% |
| THCV | | | | | | | | | |
| CBDV | | | | | | | | | |
| CBN | | | | | | | | | |
| CBG | | | | | | | | | |
| CBDA | | | | | | | | | |
| THCA | | | | | | | | | |
| Terpenoids | Total | 14 | 100% | 58% | 18% | | | ≥ 30% to ≤ 65% | ≥ 15% to ≤ 60% |
| B-Caryophyllene | | | | | | | | ≥ 6% to ≤ 65% | ≥ 1% to ≤ 25% |
| Linalool | | | | | | | | ≥ 6% to ≤ 65% | ≥ 1% to ≤ 25% |
| D-Limonene | | | | | | | | ≥ 6% to ≤ 65% | ≥ 1% to ≤ 25% |
| B-Mycene | | | | | | | | ≥ 6% to ≤ 65% | ≥ 1% to ≤ 25% |
| A-Pinene | | | | | | | | ≥ 6% to ≤ 65% | ≥ 1% to ≤ 25% |
| Humulene | | | | | | | | ≥ 6% to ≤ 70% | ≥ 2% to ≤ 25% |
| Guanine | | | | | | | | ≥ 6% to ≤ 65% | ≥ 1% to ≤ 25% |
| Active Ingredients | Total | 24 | | 100% | 32% | | | | ≥ 27% to ≤ 40% |
| Excipient Inactive | Total | 76 | | | 68% | | | | ≥ 60% to ≤ 73% |

700   702

| 1:20 | | Actual | | | | | Range | | |
|---|---|---|---|---|---|---|---|---|---|
| Ingredient | UNIT OF MEASURE (mg PER 1 mL) | % of CATEGORY (Either Cannabinoid or Terpenoid) | % of ACTIVE Ingredients (Cannabinoid AND Terpenoid) | % of TOTAL (Active & Inactive mg per 1 mL) Ingredients | | UNIT OF MEASURE (mg PER 1 mL) | % of CATEGORY (Either Cannabinoid or Terpenoid) | % of ACTIVE Ingredients (Cannabinoid AND Terpenoid) | % of TOTAL (Active & Inactive mg per 1 mL) Ingredients |
| Cannabinoids Total | 10 | 100% | 45% | 13% | | | | ≥ 30% to ≤ 60% | ≥ 9% to ≤ 25% |
| CBD | 0.5 | 5% | 2% | 1% | | | ≥ 0.4% to ≤ | ≥ 1% to ≤ 10% | ≥ 1% to ≤ 10% |
| THC | 9.5 | 95% | 43% | 12% | | | ≥ 80% to ≤ | ≥ 30% to ≤ 55% | ≥ 7% to ≤ 15% |
| THCV | | | | | | | | | |
| CBDV | | | | | | | | | |
| CBN | | | | | | | | | |
| CBG | | | | | | | | | |
| CBDA | | | | | | | | | |
| THCA | | | | | | | | | |
| Terpenoids Total | 12 | | 55% | 15% | | | | ≥ 40% to ≤ 70% | ≥ 5% to ≤ 25% |
| B-Caryophyllene | | | | | | | | ≥ 6% to ≤ 70% | ≥ 2% to ≤ 25% |
| Linalool | | | | | | | | ≥ 6% to ≤ 70% | ≥ 2% to ≤ 25% |
| D-Limonene | | | | | | | | ≥ 6% to ≤ 70% | ≥ 2% to ≤ 25% |
| B-Mycene | | | | | | | | ≥ 6% to ≤ 70% | ≥ 2% to ≤ 25% |
| A-Pinene | | | | | | | | ≥ 6% to ≤ 70% | ≥ 2% to ≤ 25% |
| Humulene | | | | | | | | ≥ 6% to ≤ 70% | ≥ 2% to ≤ 25% |
| Guanine | | | | | | | | ≥ 6% to ≤ 70% | ≥ 2% to ≤ 25% |
| Active Ingredients Total | 22 | | 100% | 28% | | | | | ≥ 15% to ≤ 30% |
| Excipient Inactive Total | 78 | | | 72% | | | | | ≥ 70% to ≤ 85% |

FIG. 8

| Changes in Seizure Frequency with Cannabinoid-Terpenoid Therapy | | | | |
|---|---|---|---|---|
| Month 3 | Dogs | Percent of All Dogs | Cats | Percent of All Cats |
| | n=179 | | n=24 | |
| | | | | |
| | | | | |
| Response rate (>50% reduction) [% of total] | 0 | 0% | 0 | 0% |
| Response rate (>70% reduction) [% of total] | 2 | .1% | 2 | 8% |
| Response rate (>90% reduction) [% of total] | 18 | 11% | 7 | 29% |
| Seizure free (%) | 159 | 97% | 15 | 63% |
| | | | | |
| | | | | |

FIG. 9

Recommended Dose for 50 lb dog

| | Individual Cannabinoids Generally Guidlines (GG) Dose in mg | | Cannabinoid - Terpinoid Solution (CTS) | | | | | | Dosage Comparison CTS to GG | | | | | |
|---|---|---|---|---|---|---|---|---|---|---|---|---|---|---|
| | | | 20:1 Dose in mg | | 4:1 Dose in mg | | 1:1 Dose in mg | | GG as a multiple of 20:1 CTS | | GG as a multiple of 4:1 CTS | | GG as a multiple of 1:1 CTS | |
| | Low | High | Low | High | Low | High | Low | High | Low | High | Low | High | Low | High |
| THC | 2.27 | 5.67 | 0.24 | 0.47 | 1.0 | 2 | 1.0 | 2 | 9.7 | 12.1 | 2.3 | 2.8 | 2.3 | 2.8 |
| CBD | 2.27 | 11.35 | 4.65 | 9.3 | 4.0 | 8 | 1.0 | 2 | 0.5 | 1.2 | 0.6 | 1.4 | 2.3 | 5.7 |

| | Individual Cannabinoids Generally Guidlines (GG) Dose in mg | | Cannabinoid - Terpinoid Solution (CTS) | | | | | |
|---|---|---|---|---|---|---|---|---|
| mg / kg / day | Low | High | 20:1 Dose in mg | | 4:1 Dose in mg | | 1:1 Dose in mg | |
| | | | Low | High | Low | High | Low | High |
| THC | 0.10 | 0.25 | 0.01 | 0.02 | 0.04 | 0.09 | 0.04 | 0.09 |
| CBD | 0.10 | 0.50 | 0.20 | 0.41 | 0.18 | 0.35 | 0.04 | 0.09 |

The Generally Guidlines (GG) dose is between 1.2 to 12.1 times the CTS dose
The CTS effective dose is many times lower than the GG total cannabinoid dose

| 22.7 | Range in mg / kg / day | | | | Comparison | |
|---|---|---|---|---|---|---|
| | GG | | CTS | | GG as multiple of CTS | |
| | Low | High | Low | High | Low | High |
| THC | 0.1 | 0.2 | 0.0 | 0.1 | 10.0 | 2.8 |
| CBD | 0.1 | 0.5 | 0.0 | 0.4 | 2.5 | 1.2 |
| Total Cannabinoids | 0.2 | 0.7 | 0.1 | 0.5 | 4.0 | 1.5 |

The effective dose of CTS is 2.8 to 10 times smaller than the GG for THC
The effective dose of CTS is 1.2 to 2.5 times smaller than the GG for CBD In sum, when taking the CTS the effective dose of total cannibinoids is 1.5 to 4 times smaller than if

FIG. 10

| Demographic and Baseline Characteristics | | | |
|---|---|---|---|
| | Cannabinoid-Terpenoid Solution | CBD Isolate | Total |
| | n=179 (per cent) | n=40 (per cent) | n=219 (per cent) |
| Sex | | | |
| Female | 87 (48.6) | 20 (50.4) | 107 (48.9) |
| Male | 92 (51.4) | 20 (49.6) | 112 (51.1) |
| Age (years) | | | |
| Mean (sd) | 6.5 (2.7) | 6.4 (3.3) | 6.4 (3.1) |
| Median (range) | 6 (2%-14%) | 6 (2% - 17%) | 6 (2% - 17%) |
| Reproductive status | | | |
| Castrated | 72 (40.2) | 16 (39.2) | 88 (40.2) |
| Spayed | 65 (36.6) | 14 (36.1) | 79 (36.1) |
| Neither | 42 (23.2) | 10 (24.7) | 52 (23.7) |
| Signs of Anxiety in Behavioral History | | | |
| Freezing | 25 (14.1) | 5 (13.7) | 30 (13.7) |
| Pacing | 78 (43.4) | 17 (42.1) | 95 (43.3) |
| Refusing to eat | 58 (32.2) | 14 (34.1) | 72 (32.9) |
| Panting | 73 (40.7) | 17 (41.4) | 90 (41.1) |
| Trembling | 86 (48.2) | 20 (49.4) | 106 (48.4) |
| Trying to Hide | 62 (34.5) | 13 (31.3) | 75 (34.2) |
| Trying to Escape | 45 (25.3) | 10 (24.8) | 55 (25.1) |
| Inapprop. urination | 11 (6.1) | 2 (5.4) | 13 (5.9) |
| Inapprop. defecation | 1 (0.3) | 0 (0.5) | 1 (0.5) |
| Salivating | 37 (20.8) | 9 (22.8) | 46 (21.0) |
| Vocalizing | 44 (24.6) | 10 (26.1) | 54 (24.7) |

FIG. 11

| | | Overall Treatment Effect on Dog Behavior | | | |
|---|---|---|---|---|---|
| | | Cannabinoid-Terpenoid Solution | | CBD oil (less than 0.03% THC) | |
| | | Primary Analysis n=179 | Sensitivity Analysis n=171* | Primary Analysis n=40 | Sensitivity Analysis n=33* |
| Score | Effect | n (per cent) | n (per cent) | n (per cent) | n (per cent) |
| 1 | Excellent | 139 (77) | 129 (75.7) | 4 (9.2) | 3 (8.2) |
| 2 | Good | 36 (21) | 35 (20.6) | 6 (14.4) | 4 (13.0) |
| 3 | Some | 4 (2.2) | 6 (3.7) | 22 (55.1) | 19 (56.4) |
| 4 | None | 0 (0) | 0 (0) | 7 (16.8) | 6 (17.1) |
| 5 | Negative | 0 (0) | 0 (0) | 2 (4.5) | 2 (5.3) |
| * Dogs that showed signs of sedation were excluded | | | | | |

FIG. 12

| Pet Owner's Score to Assess Treatment Effect | | |
|---|---|---|
| Score | Effect | Description |
| 1 | Excellent | The dog does not react to fireworks with anxious / fearful behavior at all. |
| 2 | Good | The dog's reactions are mild and the dog can calm down |
| 3 | Some | The dog's reactions are milder than usual but it cannot calm down |
| 4 | None | There is no reduction or change in the dog's reaction compared to previous occassions |
| 5 | Negative | The dog's reaction is stronger than on previous occassions |

* Dogs that showed signs of sedation were excluded

FIG. 13

| Reduction of Anxiety | | |
|---|---|---|
| Cannabinoid-Terpenoid Compound Therapy | | |
| July 4th | Dogs | Percent of All Dogs |
|  | n=179 |  |
|  |  |  |
| Good to excellent response (% of total) | 175 | 98% |
| Some response (% of total) | 4 | 2% |
| No reponse (% of total) | 0 | 0% |
| Negative response (% of total) | 0 | 0 |

FIG. 14

| Dog Characteristic | Count |
|---|---|
| Median (range) age at start of study | 8 (6-12) |
| No. of dogs by reproductive status | 38 |
|   Castrated male | 22 |
|   Spayed female | 16 |
| Breed | |
|   Golden Retriever | 5 |
|   Labrador | 5 |
|   Rottweiler | 3 |
|   German Shepherd | 4 |
|   Border Collie | 3 |
|   English Springer | 1 |
|   Springer Spaniel | 3 |
|   Boxer | 3 |
|   West Highland Terrier | 1 |
|   Crossbreds | 3 |
|   Staffordshire Bull Terrier | 1 |
|   Yorkshire Terrier | 2 |
|   Cocker Spaniel | 2 |
|   Mix | 4 |
| Median (range) body weight (lbs) | 53 (11-126) |
| No of dogs by condition | |
|   Mild | 5 |
|   Moderate | 23 |
|   Severe | 10 |

| Cat Characteristic | Count |
|---|---|
| Median (range) age at start of study | 9 (7-13) |
| No. of cats by reproductive status | 24 |
|   Castrated male | 11 |
|   Spayed female | 13 |
| Breed | |
|   Domestic Shorthair | 6 |
|   Ragdoll | 4 |
|   Maine Coon | 1 |
|   Persian | 5 |
|   Siamese | 3 |
|   Abyssinian | 1 |
|   Mix | 4 |
| Median (range) body weight (lbs) | 10 (8-12) |
| No of cats by condition | |
|   Mild | 6 |
|   Moderate | 10 |
|   Severe | 8 |

FIG. 17

|  | Canine Brief Pain Index Mean Score for All Dogs | | | |
| --- | --- | --- | --- | --- |
|  | Week 0 | Week 4 | Week 8 | Week 12 |
| CBPI Pain (0-40) | 24 | 11 | 10 | 4 |
| CBPI Activity Interference (0-60) | 38 | 17 | 14 | 6 |
| CBPI Quality of Life (0-5) | 2 | 4 | 5 | 5 |

Four domains involve pain severity: the owner assigns a numerical rating score of 0 (no pain) to 10 (severe pain) to the pet's Worst, Least, Current, and Average pain over the previous 7 days.

Six domains involve pain interference with function: the owner assigns a 0 (no interference) to 10 (complete interference) to General Activity, Enjoyment of Life, Ability to Rise to Standing, Ability to Walk, Ability to Run, and Ability to Climb Stairs.

The final domain involves quality of life: the owner assesses the dog's general quality of life from 0 (poor) to 5 (excellent)

FIG. 19

COMPOUND AND METHOD FOR TREATING DISEASES AND DISORDERS

PRIORITY CLAIM

The present application is a Non-Provisional Utility Patent Application of U.S. Provisional Application No. 62/867,116, filed on Jun. 26, 2019, entitled, "Solution and Method for Treating Certain Conditions with Cannabinoids."

BACKGROUND OF THE INVENTION

Field of Invention

The present invention relates to pharmaceutical compounds and methods for treating and/or preventing diseases and disorders and, more particularly, to a cannabinoid-terpenoid solution (CTS) and method of treating a disease state or condition in mammals other than humans via cannabinoid-terpenoid therapy.

Description of Related Art

Cannabidiol (CBD) is the second of the most prevalent active ingredients found in *cannabis*. CBD as used for pets is widely available, yet also widely misunderstood. For example, there is a general confusion over hemp-based CBD and whole-flower CBD. There is also confusion over state and federal laws concerning CBD use in foods, medicinal and naturopathic products. Additionally, many CBD products for animals barely contain any of the CBD claimed and, if they do actually contain CBD, the products are often not tested for purity or content. The CBD available for pets is provided only for oral administration in an inconsistent and wide range of doses, which are not well-absorbed.

Compounding the lack of clarity regarding the use of *cannabis* in pet medicine is the prevailing information about tetrahydrocannabinol (THC) being toxic for animals, dogs especially. Combined with the fact that many of the terpenoids found in essential oils are toxic to felines, terpenoids do not stand out as obvious or even likely candidates for medicinal formulations for companion animals. It was even believed that terpenoids modulate the effect of CBD and THC at the body's CB1 and CB2 cannabinoid receptors, thereby providing an inhibiting effect on THC intoxication (see the List of Incorporated Literature References, Literature Reference No. 1); however, a recent study called these findings into question, finding that they do not modulate the effects of THC and CBD at those receptors (see Literature Reference No. 2).

There is thus a need for a cannabinoid-terpenoid medication for animals - one that is standardized in composition, formulation and dose, administered by means of an appropriate delivery system - so that it can be used in clinical trials and provide consistent, safe, effective medicine to patients. While each of the top 25 drugs approved for use in humans were tested on animals, those tests had to do with toxicity and not effectiveness in either the animals or humans. Further, due to the high cost of drug development, few drugs are developed specifically for animals. Most of the drugs approved for veterinary care for the treatment of conditions such as epilepsy, cancer, osteoarthritis, and anxiety have a high enough toxicity that using them is often a trade-off between improving one condition, but suffering other, potentially equally or more distressing side-effects.

While CBD treats for pets have been all the rage in recent times, the use of medical *cannabis* for pets has been steeped in undeserved controversy, thanks in large part to the government's mis-classification of *cannabis* as a Schedule 1 substance (a designation reserved for drugs having "no medicinal value") coupled with a lack of clinical study, little reliable data and therefore a general lack of acceptance within the medical establishment. *Cannabis* is perhaps the most powerful and effective medicine, offering wide-ranging application and possibility for future discoveries, yet it is not embraced by the larger medical community.

Meanwhile, the evidence in humans is overwhelming that *cannabis* can relieve certain types of pain, nausea, and other symptoms caused by a variety of diseases or by the harsh drugs sometimes used to treat them. *Cannabis* has proven less toxic and more effective than many of the drugs veterinarians prescribe every day. For example, Tramadol is an opioid drug which works well via intravenous delivery during and immediately post-surgery to control pain, but fails to control post-surgical pain at home effectively when taken in pill form and creates more toxicity than relief, often requiring close monitoring of the animal's liver and kidney function and frequent trips to the veterinarian. The way that canines absorb and metabolize oral Tramadol may hinder the drug's pain-reducing effects.

The endocannabinoid system has been found to be pervasive in mammalian species. It has also been described in invertebrate species as primitive as the Hydra. Insects, apparently, are devoid of this, otherwise, ubiquitous system that provides homeostatic balance to the nervous and immune systems, as well as many other organ systems. The endocannabinoid system (ECS) has been defined to consist of three parts, which include (1) endogenous ligands, (2) G-protein coupled receptors (GPCRs), and (3) enzymes to degrade and recycle the ligands. Two endogenous molecules have been identified as ligands in the ECS to date. The endocannabinoids are anandamide (arachidonoyl ethanolamide) and 2-AG (2-arachidonoyl glycerol). Two G-coupled protein receptors (GPCR) have been described as part of this system, with other putative GPC being considered.

Coincidentally, the phytochemicals produced in large quantities by the *cannabis* sativa L plant, and in lesser amounts by other plants, can interact with this system as ligands. These plant-based cannabinoids are termed phytocannabinoids. The precise determination of the distribution of cannabinoid receptors in animal species is an ongoing project, with the canine cannabinoid receptor distribution currently receiving the most interest in non-human animals.

The ECS was discovered secondary to the discovery of the structure of the psychotropic phytocannabinoid, -Δ-9-tetrahydrocannabinol (THC). Cannabinoid receptor 1 was found during the search for the biological target(s) for THC (see Literature Reference No. 3). THC is the only psychotropic cannabinoid foundin *Cannabis* sativa L and is responsible for some of this plant's biomedical activity. The non-psychotropic cannabinoids such as CBD, Cannabigerol (CBG), Cannabichromene (CBC), other minor cannabinoids, terpenes, and flavonoids have been found to have comparable biomedical activity to that of THC without its side-effect of intoxication.

Studies at the National Institute on Drug Abuse in Bethesda, Maryland cloned the G-coupled protein receptor (GPCR) in 1990, which is the target for endogenous cannabinoid ligands, and named it, "Cannabinoid Receptor 1 (CB1). This receptor belongs to the Class A rhodopsin-like family of GPCRs (see Literature Reference No. 4). A few years later, the second GPCR: "Cannabinoid Receptor 2" (CB2) was cloned (see Literature Reference No. 45). The CB1 and the CB2 receptors participate in numerous essential biological processes. Some of these are: Neuronal plasticity, pain, anxiety, inflammation, neuro-inflammation, immune function, metabolic regulation, and bone growth (see Literature Reference Nos. 6 through 14, respectively).

There is a paucity of studies in veterinary species regarding the relationship between the endocannabinoid system and specific diseases. The existing published studies have focused on the human animal or have utilized laboratory animal experimental models. The animal experiments for human medicines are focused on toxicity rather than efficacy of the medicine for humans or animals. Thus, there is a significant need for clinical studies in veterinary species to provide evidence-based applications for phytocannabinoid and endocannabinoid molecules (see Literature Reference No. 15).

One interspecies variation in the anatomical location of the CB1 receptors is found in dogs. As compared to humans, studies have determined the number of CB1 receptors in hind brain structures in the dog to far exceed those found in the human animal. The US government conducted studies that determined that dogs have large numbers of cannabinoid receptors in the cerebellum, brain stem, and medulla oblongata (see Literature Reference No. 16). Other locations for CB1 include the peripheral nervous system, as well as cardiovascular, immune, gastrointestinal, and reproductive tissues. CB2 has been found mainly in cells of the immune system and the spleen and tonsils (see Literature Reference No. 18). The CB1 and CB2 receptors are structurally quite similar, despite their different anatomical locations in the central nervous and immune systems, respectively.

"Static ataxia," which is a unique neurological reaction to THC in the dog, is explained by this high concentration of CB receptors in the cerebellum. Dogs in particular will suffer from "Static Ataxia" upon exposure to THC at doses >0.5 mg/kg IV (see Literature Reference No. 17).

Dogs have a higher number of endocannabinoid receptors in their cerebellum and brain stem (see Literature Reference No. 19). These parts of the brain control coordination, heart rate, respiratory rate, etc. This makes dogs particularly susceptible to toxicity from too much THC. Dogs intoxicated with THC may show signs of static ataxia. These dogs will seem rigid and have difficulty standing. This condition is unique to dogs and, while not fatal, often requires supportive medical therapy and intervention. While a toxic overdose is possible, orally ingested *cannabis* has no known $LD_{50}$ in dogs. (see Literature Reference No. 20). The name $LD_{50}$ is an abbreviation for "Lethal Dose, 50%" or median lethal dose. It is the amount of the substance required (usually per body weight) to kill 50% of the test population. Thus, while dogs are susceptible to toxicity from too much THC and may need support and intervention, there is currently no measured $LD_{50}$ for the canine population when ingesting THC; nevertheless, ingested *cannabis* is known to be potentially toxic to animals and canines.

Thus, a continuing need exists for a cannabinoid-terpenoid medication for animals - one that is standardized in composition, formulation and dose, administered by means of an appropriate delivery system so that it can be used to provide consistent, safe, effective medicine to patients. Such a formulation desirably improves upon on the prior art by offering a formulation standardizing the ratios of active ingredients including CBD, THC, other cannabinoids and terpenoids. A continuing need also exists for a specific method of delivery which delivers a therapeutic dose balanced with animal safety, as well as a system for generating a master clinical database that gathers patient data to monitor and update dosage, among other functions.

SUMMARY OF INVENTION

The present invention relates to a lipophilic pharmaceutical formulation and method of treating a disease state or condition in mammals other than humans via cannabinoid-terpenoid therapy. More specifically, the present disclosure provides a cannabinoid-terpenoid solution (CTS) for use in the administration of a cannabinoid-terpenoid medicament in a mammal and a method for treating such an animal using the CTS. Described below are several specific aspects or embodiments according to the principles of the present invention. It should be understood that while several aspects or embodiments are provided, the invention is not intended to be limited thereto as other components may be added, exchanged and/or removed in accordance with the principles herein. Further, it should also be understood that the terms "aspect" or "embodiment" are used interchangeably herein.

In one aspect or embodiment, the CTS comprises two or more cannabinoids and one or more terpenes (collectively referred to herein as terpenoids).

In yet another aspect, the two or more cannabinoids comprise at least two cannabinoids selected from a group consisting of cannabidiol (CBD), tetrahydrocannabinol (THC), cannabigerol (CBG), cannabinol (CBN), cannabichromene (CBC), cannabidivarin (CBDV), cannabidiolic acid (CBDA), tetrahydrocannabivarin (THCV), and tetrahydrocannabinolic acid (THCA).

In another aspect, a lipophilic carrier is mixed with the two or more cannabinoids and the one or more terpenes.

In another aspect, the two or more cannabinoids collectively comprise an amount less than or equal to 40 percent of the CTS, wherein the one or more terpenes comprise an amount less than or equal to 60 percent of the CTS, and wherein the lipophilic carrier comprises an amount less than or equal to 85 percent of the CTS.

In yet another aspect, the two or more cannabinoids comprise at least CBD and THC, and wherein the CBD comprises between 7 percent and 15 percent of the CTS and the THC comprises between 0.1 and 10 percent of the CTS, thereby forming a CBD dominant compound.

In another aspect, the CBD comprises between 10 percent and 14 percent of the CTS and the THC comprises between 0.3 percent and 1 percent of the CTS, thereby forming a CBD dominant compound.

In yet another aspect, the one or more terpenes comprise between 13 and 17 percent of the CTS.

In another aspect, the two or more cannabinoids comprise at least CBD and THC, and wherein the CBD comprises between 7 percent and 30 percent of the CTS and the THC comprises between 1 and 10 percent of the CTS, thereby forming a CBD rich compound.

In another aspect, the CBD comprises between 8 percent and 12 percent of the CTS and the THC comprises between 2 percent and 4 percent of the CTS, thereby forming a CBD rich compound.

In another aspect, the one or more terpenes comprise between 16 and 20 percent of the CTS.

In yet another aspect, the two or more cannabinoids comprise at least CBD and THC, and wherein the CBD comprises between 1 percent and 5 percent of the CTS and the THC comprises between 1 and 5 percent of the CTS, thereby forming a CBD:THC balanced compound.

In another aspect, the CBD comprises between 2 percent and 4 percent of the CTS and the THC comprises between 2 percent and 4 percent of the CTS, thereby forming a CBD:THC balanced compound.

In another aspect, the one or more terpenes comprise between 18 and 22 percent of the CTS.

In another aspect, the two or more cannabinoids comprise at least CBD and THC, and wherein the THC comprises between 7 percent and 30 percent of the CTS and the CBD comprises between 1 and 10 percent of the CTS, thereby forming a THC rich compound.

In yet another aspect, THC comprises between 9 percent and 15 percent of the CTS and the CBD comprises between 2 percent and 4 percent of the CTS, thereby forming a THC rich compound.

In another aspect, the one or more terpenes comprise between 16 and 21 percent of the CTS.

Further, in another aspect, the two or more cannabinoids comprise at least CBD and THC, and wherein the THC comprises between 7 percent and 15 percent of the CTS and the CBD comprises between 0.2 and 10 percent of the CTS, thereby forming a THC dominant compound.

In another aspect, the THC comprises between 10 percent and 14 percent of the CTS and the CBD comprises between 0.3 percent and 2 percent of the CTS, thereby forming a THC dominant compound.

In another aspect, the one or more terpenes comprise between 16 and 20 percent of the CTS.

In another aspect, the THC comprises between 8 percent and 12 percent of the CTS and the CBD comprises between 2 percent and 4 percent of the CTS, thereby in another aspect, the one or more terpenes comprise between 13 and 17 percent of the CTS.

In another aspect, the one or more terpenes is one or more terpenes selected from a group consisting of Beta-Carophyllene, Linalool, D-Limonene, Beta-Myrcene, Alpha-Pinene, Humulene, and Guanine, or any combination thereof.

In yet another aspect, the one or more terpenes include one or more terpenes selected from a group consisting of Beta-Carophyllene, Linalool, D-Limonene, Beta-Myrcene, Alpha-Pinene, Humulene, and Guanine, or any combination thereof, to collectively form between 10 percent and 20 percent of the CTS.

In another aspect, the one or more terpenes collectively form between 12 percent and 18 percent of the CTS.

In another aspect, the lipophilic carrier is a medium chain triglyceride (MCT) oil.

In another aspect, at least one of the two or more cannabinoids is a highly purified extract of *cannabis* which comprises at least 90% Δ9-tetrahydrocannabinol (THC).

In another aspect, at least one of the two or more cannabinoids is a highly purified extract of *cannabis* which comprises at least 90% cannabidiol CBD.

In another aspect, at least one of the one or more terpenes is a highly purified extract which is selected from a group consisting of Beta-Carophyllene, Linalool, D-Limonene, Beta-Myrcene, Alpha-Pinene, Humulene, and Guanine.

In another aspect, at least one of the two or more cannabinoids is in a form selected from a group consisting of being derived from hemp and being synthetic.

In another aspect, the CTS comprises at least 5% CBD.

In another aspect, the CTS comprises at least 5% THC.

In another aspect, the CTS comprises at least 5% of one or more terpenes.

In another aspect, the two or more cannabinoids include CBD and THC, such that the CTS comprises less than 0.3% THC.

In another aspect, the non-human animal is a mammal selected from a group consisting of a canine, a feline, an equine, a cow, a goat, a sheep, a lamb, a monkey, an ape, and a pig.

In yet another aspect, the CTS comprises two or more cannabinoids, the two or more cannabinoids comprising at least two cannabinoids selected from a group consisting of cannabidiol (CBD), tetrahydrocannabinol (THC), cannabigerol (CBG), cannabinol (CBN), cannabichromene (CBC), cannabidivarin (CBDV), cannabidiolic acid (CBDA), tetrahydrocannabivarin (THCV), and tetrahydrocannabinolic acid (THCA). Further, the two or more cannabinoids include at least CBD and THC, such that CBD and THC are mixed within the CTS to form a ratio with respect to one another, the ratio being selected from a group consisting of CBD dominant, CBD rich, CBD:THC balanced, THC rich, and THC dominant. Additionally, and in another aspect, one or more terpnes are mixed with the two or more cannabinoids.

The present disclosure also provides a method for treating a disease, state or disorder in a non-human animal, comprising an act of administering the CTS to an animal suffering from a disease, state or disorder, the CTS comprising two or more cannabinoids and one or more terpenes.

In another aspect, a lipophilic carrier is mixed with the two or more cannabinoids and the one or more terpenes.

In another aspect, the disease, state, or disorder is selected from a group consisting of epilepsy, anxiety, pain, inflammation, degenerative myelopathy, Parkinson's disease, lameness and gait issues, elbow dysplasia, hip dysplasia, back and hind leg problems, arthritis, seizures, encephalopathy, lethargy, focus/attentional problems, and cognitive issues, spasticity, cancer, glioblastoma, weakness, numbness, mood disorders, hypertension, tremors, peripheral neuropathy, bowel and bladder control issues, inactivity, poor appetite, tumors, Cushing's disease, aggressive behavior, pruritus, dermatitis, vomiting, nausea, glaucoma, noise aversion, dystonia, personality change, restlessness, inflammatory bowel syndrome, and neurological damage.

The present disclosure also provides a method for treating idiopathic epilepsy in a non-human animal, comprising and act of administering the cannabinoid-terpenoid medicament CTS to an animal suffering from idiopathic epilepsy, the cannabinoid-terpenoid medicament CTS comprising two or more cannabinoids and one or more terpenes.

In another aspect, in administering the CTS to the animal, the CTS is administered in combination with one or more concomitant anti-epileptic drugs (AED). Further, the AED is selected from a group consisting of Phenobarbital, Potassium Bromide, Levetiracetam, Zonciamide and Gabapentin.

In yet another aspect, in administering the CTS to the animal, the CTS is administered orally to allow for oral mucosal delivery to be immediately absorbable by the mammal to treat idiopathic epilepsy.

In yet another aspect, in administering the CTS to the animal, the CTS is administered to the surface of the palatal, lingual, sublingual, gingival, labial, pharyngeal or buccal mucosa, or combinations thereof.

In yet another aspect, in administering the CTS to the animal, the CTS is administered through a spray on oral mucosa.

In yet another aspect, in administering the CTS to the animal, the CTS is administered to oral mucosa via a syringe.

The present disclosure also provides a method for treating anxiety in a non-human animal, comprising an act of administering a cannabinoid-terpenoid medicament CTS to an animal suffering from anxiety, the cannabinoid-terpenoid medicament CTS comprising two or more cannabinoids and one or more terpenes.

Further, in administering the CTS to the animal, the CTS is administered orally to allow for oral mucosal delivery to be immediately absorbable by the animal to treat anxiety. In another aspect, in administering the CTS to the animal, the CTS is administered to the surface of the palatal, lingual, sublingual, gingival, labial, pharyngeal or buccal mucosa, or combinations thereof. Or in yet another aspect, the CTS is administered onto an area between a cheek and gums of the animal for increasing delivery The present disclosure also provides a method for treating pain or inflammation in a non-human animal, comprising an act of administering a cannabinoid-terpenoid medicament CTS to an animal suffering from pain or inflammation, the cannabinoid-terpenoid medicament CTS comprising two or more cannabinoids and one or more terpenes. In yet another aspect, in administering the CTS to the animal, the CTS is administered orally to allow for oral mucosal delivery to be immediately absorbable by the animal to treat pain or inflammation.

Finally, as can be appreciated by one in the art, the present invention also comprises a method for forming and using the invention as described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 1 is a table depicting cannabinoid-terpenoid solution (CTS) active ingredients according to various embodiments of the present invention;

FIG. 2 is a table depicting various benefits of the CTS as related to the terpenoids and surprising results;

FIG. 3 is a table depicting example cannabinoid-terpenoid structures according to various embodiments of the present invention;

FIG. 4 is a chart depicting a formulation of a CTS according to various embodiments of the present invention, depicting an aspect in which a cannabidiol (CBD) is considerably more present than tetrahydrocannabinol (THC) within the compound to form a CBD dominant compound;

FIG. 5 is a chart depicting a formulation of a CTS according to various embodiments of the present invention, depicting an aspect in which CBD is slightly more present than THC within the compound to form a CBD rich compound;

FIG. 6 is a chart depicting a formulation of a CTS according to various embodiments of the present invention, depicting an aspect where the amount of CBD is approximately the same as that of THC within the compound to form a balanced compound;

FIG. 7 is a chart depicting a formulation of a CTS according to various embodiments of the present invention, depicting an aspect in which THC is slightly more present than CBD within the compound to form a THC rich compound;

FIG. 8 is a chart depicting a formulation of a CTS according to various embodiments of the present invention, depicting an aspect in which THC is considerably more present than CBD within the compound to form a THC dominant compound;

FIG. 9 is a table depicting experimental results of using a CTS according to the principles of the present invention in treating epilepsy in dogs;

FIG. 10 is a table comparing dosages of the CTS against those of generally accepted doses;

FIG. 11 is a table depicting demographics and baseline characteristics of the animals as used in the experimental studies described herein;

FIG. 12 is a table depicting overall treatment effect on dog behavior;

FIG. 13 is a table depicting pet owner scores for assessing the effects of treatment using a CTS according to the principles of the present invention;

FIG. 14 is table depicting experimental results showing a reduction in anxiety using a CTS according to the principles of the present invention;

FIG. 17 is a table depicting the characteristics of study participants;

FIG. 19 is a table depicting experimental results of using a CTS according to the principles of the present invention in treating pain and inflammation in dogs.

DETAILED DESCRIPTION

Figure 15:
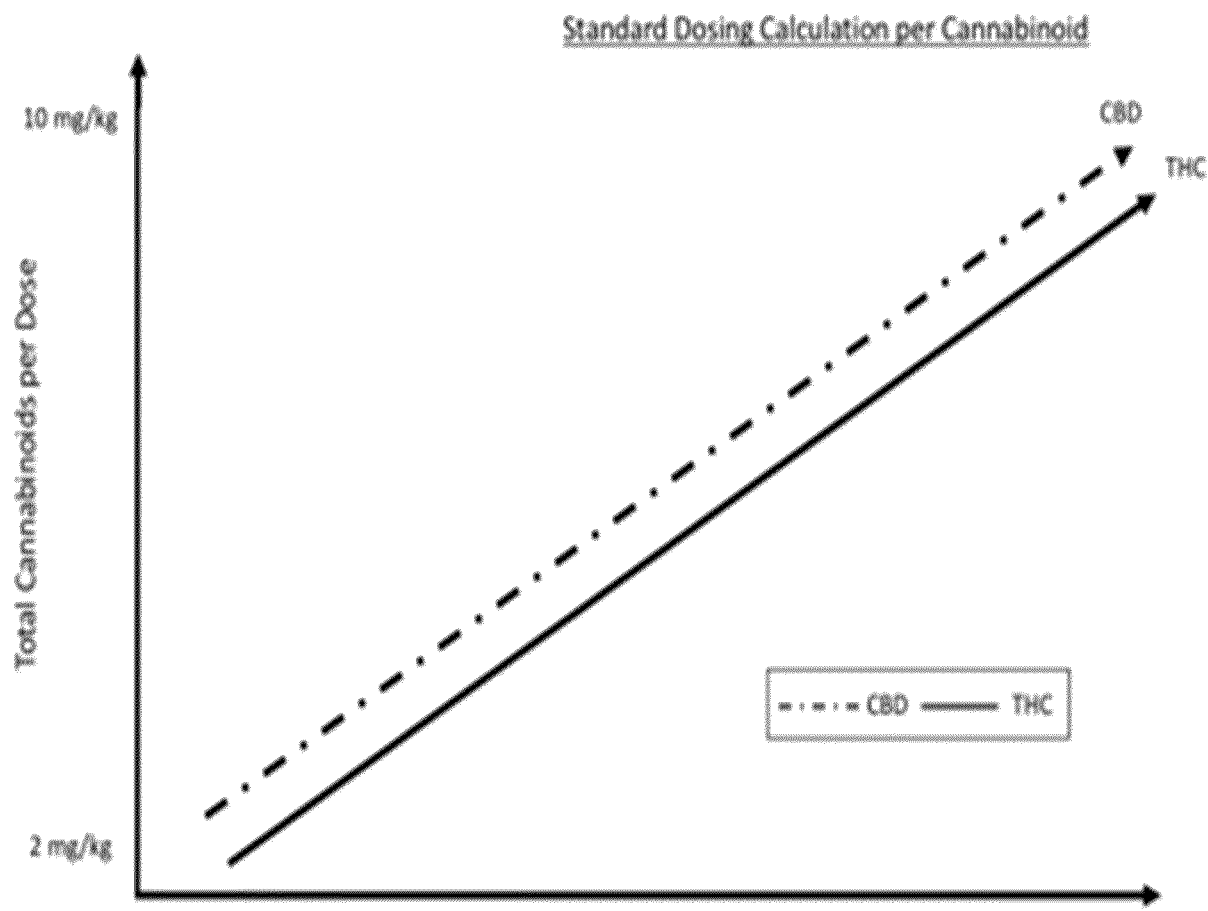
FIG. 15 is a graph depicting that given the common CBD and THC companion animal and human dose guidance, the overall cannabinoid amount per dose increases as THC increases.

The present invention relates to pharmaceutical compounds and methods for treating and/or preventing diseases and disorders and, more particularly, to a lipophilic pharmaceutical formulation and method of treating a disease state or condition in mammals other than humans via cannabinoid-terpenoid therapy. Also described in this disclosure is a database collection and generation system that receives experimental and/or clinical data to ensure accurate compound dosing and treatments.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention. Further, unless the context requires otherwise, all percentages referred to herein are percentages by weight of the composition. Unless the context requires otherwise, all amounts referred to herein are intended to be amounts by weight. Further, unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described. Where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Provided below are specific details regarding various embodiment of the present invention. Following the specific details is a glossary of terms used in the description and claims, following by a listing of incorporated and cited literature references.

Specific Details

As referenced above, CBD and THC have been shown to have medicinal benefits in humans and, in the cases of CBD, anecdotally, in non-human mammals. While some benefits have been shown, a known issue in the prior art is the toxicity of the chemicals, particularly when applied to canines. The present invention improves upon the prior art by providing a cannabinoid-terpenoid solution (CTS) and method for treating ailments in mammals other than humans, by administering to the oral/buccal mucosa the CTS comprising of THC, CBD (whole flower, hemp based, single molecule, distillate or isolate, natural or synthetic); other cannabinoids; *cannabis* terpenes; non-*cannabis* terpenes; in a lipophilic solution (for example Medium Chain Triglyceride [MCT] coconut oil; *cannabis* oil, or other binders as appropriate that operate as excipients or carriers). Notably, the specific percentages and ratios of CBD, THC, and terpenes, including the specified dosages, have rendered the formula or compound both effective and safe.

The specific doses and formula (ingredients, ratio, percentage, etc.) resulting in both an effective and safe product are unique and unexpected. The various embodiments as described herein are not obvious to those skilled in the art as they were not deduced through routine optimization because of the interplay of four animal-specific reasons: (i) THC is well-known to be toxic to companion animals, especially dogs; (ii) CBD is toxic to companion animals, especially dogs, in large doses and no specific dosage or dosage range has been identified ; (iii) *Cannabis* is biphasic; (iv) Because of the entourage effect and since *cannabis* is individualized medicine, dosing is not based on weight for each individual active ingredient, as the final composition is greater than the sum of its parts; and (v) there is no dosing specification or range for the administration of a combination of two or more cannabinoids, cannabinoids combined with terpenes and / or cannabinoids administered via any specific method of delivery.

Thus and as noted above, the present disclosure is directed to a cannabinoid-terpenoid solution (CTS) and method of treating a disease state or condition in mammals other than humans via cannabinoid-terpenoid therapy (through administration of the CTS). More specifically, the present invention is directed to (A) a CTS that can be used for a variety of therapies to treat diseases and disorders, (B) a method for treating a variety of diseases and disorders using the CTS, (C) a method for increasing delivery to effectively treat the diseases and disorders, (D) a method of dosing to effectively treat the diseases and disorders and (E) a master clinical database generation and collection system that receives experimental and/or clinical data to ensure accurate compound dosing and treatments. For clarity, each of these aspects is described in turn, below.

(A) Cannabinoid-Terpenoid Solution

The present disclosure provides several embodiments of unique formulations of the CTS. It should be understood that although the present disclosure is described with respect to a "solution," the invention is not intended to be limited to a liquid or gel format. Thus, while the CTS is, in some embodiments, desirably formed as a liquid or gel, in other embodiments, the CTS can include any components as may be necessary to package or otherwise form the CTS in a solid (e.g., such as a pill) or any other suitable form for delivery. Thus, it should be understood that the term "solution" with respect to CTS can be used interchangeably with respect to the word composition or other suitable word to indicate that the components forming the solution are packaged together to form a combined product.

The formulations of the CTS have been shown to be effective and safe in treating a variety of diseases based on various ratios and formulas of the cannabinoids at least two of which are CBD, THC with the remaining active ingredients being at least one or a combination of terpenes. Although not limited thereto, the CTS is described with respect to five desired formulations and variants thereof. Specifically, and as depicted in FIGS. 4 through 8, the present disclosure provides: (1) a CBD Dominant Compound (approximately 20:1 CBD:THC ratio), (2) a CBD Rich Compound (approximately 4:1 CBD:THC ratio), (3) a Balanced Compound (approximately 1:1 CBD:THC ratio), (4) a THC Rich Compound (approximately 1:4 CBD:THC ratio), and (5) a THC Dominant Compound (approximately 1:20 CBD:THC ratio). The various CTS as presented in FIGS. 4 through 8 illustrate various ranges of CBD to THC. It should be noted that although specific ratios are presented with respect to CBD and THC, additional cannabinoids can also be added other than CBD and THC and that, in some embodiments, the ratios are not just the ratios of those two but also include one or more of the other cannabinoids listed herein. Further, although this disclosure is described in detail with respect to CBD and THC, it is also important to note that the terpenes are active ingredients that, when combined with the cannabinoids, provided safe and effective doses of the CTS. It should also be noted that the inactive ingredients, or excipients, can be any suitable excipient or carrier as desired to provide for the applicable delivery method, taste, or form of composition. Thus, various additional excipients or materials are described herein that can be used in any of the CTS as described, or any combination thereof.

The dosing range varies according to the ratio or percentages between the two cannabinoids and the ratio of the cannabinoids to one another, to the terpenoids, as well as the ratio of the active ingredients to the inactive ingredients to the inactive ingredients. Therefore, the recommended dosing range used in the examples is specific to the formulation itself (the ratio between CBD and THC) as well as the product concentration or method of administration For example, when CBD and THC are combined in the same dose, a greater reduction in pain is seen versus using the cannabinoids separately, but what also is seen is that the strength/therapeutic effect of the dose is higher overall because the two cannabinoids potentiate one another. The whole is greater than the sum of its parts. Example doses are depicted in the table as shown in FIG. 10. It is noted that, depending on the ratio, when taking the (CTS) of the present invention the effective dose of CBD in the CTS is 1.2 to 2.5 times smaller than prior art, and when taking the CTS of the present invention the effective dose of THC in the CTS is 2.8 to 10 times smaller than prior art. Moreover, the effective dose of total cannabinoids in the CTS is 1.5 to 4 times smaller than if one were to take the THC and CBD cannabinoids separately, showing a dramatic and unexpected improvement over the prior art.

As can be understood by those skilled in the art, the formulation and dosage varies based on the particular delivery method, the ailment being treated and the endocannabinoid system of the recipient. For example, for the reduction of anxiety in an equine versus a dog versus a human, both the method of delivery and the concentration of active ingredients, as well as the ingredients themselves may be different for the CTS formulated to offer relief for the same condition. While human beings and dogs both have an endocannabinoid system, dogs have a higher number of cannabinoid receptors CB1 and CB2 (receptors for THC and CBD, respectively) in the brain compared with humans and therefore require different formulations, as well as different dosing of *cannabis*-derived medicine for effectiveness, as discussed It should be noted that "psychoactive" doses not mean "high" or a reduction in cognition (executive thinking). In fact, some psychoactive substances (caffeine) can actually improve cognition. Psychoactive simply means that the substance can change brain function and results in alterations in perception, mood, consciousness, cognition, or behavior. CBD can improve mood and reduce anxiety, meaning it meets the definition of psychoactive. But, CBD does not typically make humans feel "high" or reduce overall cognition. Antidepressants and stimulant medications are also considered to be psychoactive.

Cannabinoids like CBD and THC potentiate one another. Alternatively, and as shown in FIG. 1, Cannabinoids and Terpenes have a synergistic effect. The terpene Myrcene, for example, enhances the potency of THC by making it easier for the cannabinoid to cross the blood/brain barrier. Conversely, terpenes like Pinene are said to inhibit the effects of THC. Inhibiting the psychoactive effects of THC is especially important with respect to dogs. Thus, the present disclosure provides for unique formulations using cannabinoids mixed with terpenes, several non-limiting examples of which are depicted in the table shown in FIG. 1.

The terpene Myrcene, can also reduce resistance in the blood-brain barrier, enabling easier passage of other beneficial chemicals. Pinene helps counteract compromised cognition and memory caused by THC. A combination of terpenes Pinene, Myrcene, and Caryophyllene help unravel anxiety. Mixing terpenes linalool and limonene with the cannabinoid CBG shows promise in the treatment of MRSA. THC plus CBN yields enhanced sedating effects. Linalool and limonene combined with CBD is even being examined as an anti-acne treatment.

The combination of cannabinoids mixed with terpenoids has been shown to provide several unexpected therapeutic benefits that support treatment for a variety of diseases and disorders, several of which are illustrated in the table as depicted in FIG. 2.

In certain preferred embodiments, the cannabinoid drug(s) is derived from an endocannabinoid, a phytocannabinoid, a synthetic cannabinoid, or mixtures of any of the foregoing. In certain preferred embodiments, the cannabinoids comprise CBD and THC.

In yet another aspect, THC and CBD are not the only cannabinoids envisioned for the range of medications (other cannabinoids can play an important role in the future, such as CBN, CBG, CBDA, THCA, THCV). Thus, in some aspects, THC and CBD are swapped with other cannabinoids, or any combination thereof.

Figure 3:
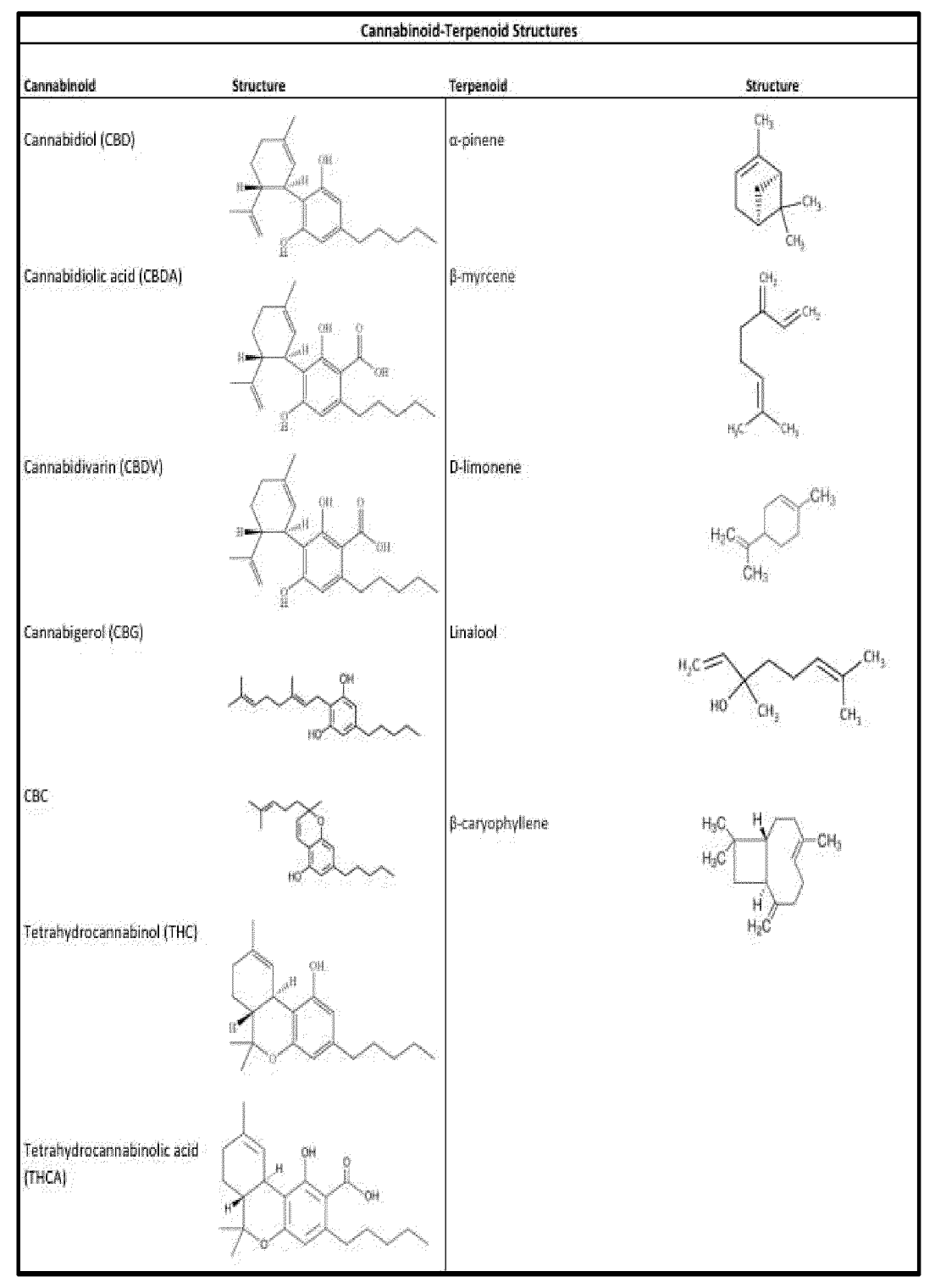

Notably and as referenced above, the formula also includes any suitable terpenes (collectively referred to herein as terpenoids or terpenes), several non-limiting examples of which are depicted in the figures submitted herewith. Several non-limiting examples of cannabinoids and terpenes as described in the present disclosure are listed in FIG. 1 along with their standard abbreviations. This is not exhaustive and merely details several example cannabinoids and terpenes which are identified in the present disclosure for reference. The structures are shown in FIG. 3. Over 100 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids). Thus, the formulations as described herein can be used any of the known cannabinoids or any combination or variant thereof, including any of phytocannabinoids, endocannabinoids and synthetic cannabinoids.

Furthermore, the CTS is formed in a form suitable for a delivery method, non-limiting examples of which include inhalation, oral, intramuscular injection, intravenous (IV)-drip, lingual, sub-lingual, nasal, anal, percutaneous transdermal absorption, and transdermal patch. One non-limiting example of such a suitable composition or solution according to the principles of the present invention are described throughout the present disclosure. For further understanding, several specific example embodiments are provided below.

As shown in FIG. 4, one embodiment according to the principles of the present invention is a CBD dominant compound. In this aspect, the formulation includes a considerably greater amount of CBD than THC, such that amount of CBD within the CTS is approximately twenty times that of THC. This particular formulation is applicable for several proven treatments, including, but not limited to restlessness, inflammatory bowel syndrome, neuroprotective effects.

It should be noted that while one specific example of a CBD dominant compound or formula is depicted and described in FIG. 4, the invention is not intended to be limited thereto as other ranges and terpenes can be included. For example, one desired embodiment includes the actual amounts 400 as depicted in the left-side of the table, while various ranges 402 in accordance with the present invention are presented on the right-side of the table. Thus, in one embodiment, the CBD dominant formulation includes the ranges 402 as depicted, while in other embodiments the ranges are decremented by a percentage point from each outer bound of the range until reaching the actual amounts 400, or any combination thereof. Further, the terpenes forming the composition can be any one or more of the listed terpenes as depicted, or any combination thereof, to total the amount of terpenoids present in the CTS. In some aspects, the terpenoids include approximately equal amounts of each of the different terpenes as listed in FIG. 4 to comprise the total amount of terpenoids present; while in other aspects, one or more of the individual terpenes are presented in greater amounts than the other terpenes.

In yet another desired aspect or embodiment, the CTS is a CBD Rich Compound (with an approximately 4:1 CBD:THC ratio). In this aspect and as shown in FIG. 5, the formulation includes a slightly greater amount of CBD than THC, such that amount of CBD within the CTS is approximately four times that of THC. This particular formulation is applicable for several treatments, including, but not limited to seizures and epilepsy.

It should be noted that while one specific example of a CBD Rich compound or formula is depicted and described in FIG. 5, the invention is not intended to be limited thereto as other ranges and terpenes can be included. For example, one desired embodiment includes the actual amounts 500 as depicted in the left-side of the table, while various ranges 502 in accordance with the present invention are presented on the right-side of the table. Thus, in one embodiment, the CBD Rich formulation includes the ranges 502 as depicted, while in other embodiments the ranges are decremented by a percentage point from each outer bound of the range until reaching the actual amounts 500, or any combination thereof. Further, the terpenes forming the composition can be any one or more of the listed terpenes as depicted, or any combination thereof, to total the amount of terpenoids present in the CTS. In some aspects, the terpenoids include approximately equal amounts of each of the different terpenes listed to comprise the total amount of terpenoids present; while in other aspects, one or more of the individual terpenes are presented in greater amounts than the other terpenes. As a non-limiting example, in one desired aspect or embodiment, all of the terpenes as listed in FIG. 5 are included, with a total percentage of Beta-Myrcene being approximately twice as much as that of the other terpenes.

In yet another desired aspect or embodiment, the CTS is a CBD:THC Balanced compound (with an approximately 1:1 CBD:THC ratio). In this aspect and as shown in FIG. 6, the formulation includes approximately equal amounts of CBD and THC. This particular formulation is applicable for several proven treatments, including, but not limited to inflammatory bowel disease.

It should be noted that while one specific example of a CBD:THC Balanced compound or formula is depicted and described in FIG. 6, the invention is not intended to be limited thereto as other ranges and terpenes can be included. For example, one desired embodiment includes the actual amounts 600 as depicted in the left-side of the table, while various ranges 602 in accordance with the present invention are presented on the right-side of the table. Thus, in one embodiment, the CBD:THC Balanced formulation includes the ranges 602 as depicted, while in other embodiments the ranges are decremented by a percentage point from each outer bound of the range until reaching the actual amounts 600, or any combination thereof. Further, the terpenes forming the composition can be any one or more of the listed terpenes as depicted, or any combination thereof, to total the amount of terpenoids present in the CTS. In some aspects, the terpenoids include approximately equal amounts of each of the different terpenes listed to comprise the total amount of terpenoids present; while in other aspects, one or more of the individual terpenes are presented in greater amounts than the other terpenes. As a non-limiting example, in one desired aspect or embodiment, all of the terpenes as listed in FIG. 6 are included, with a total percentage of Beta-Myrcene and Beta-Caryophyllene being approximately twice as much as that of the other terpenes.

As shown in FIG. 7 and in yet another desired aspect or embodiment, the CTS is a THC Rich Compound (with an approximately 1:4 THC:CBD ratio). In this aspect, the formulation includes a slightly greater amount of THC than CBD, such that amount of THC within the CTS is approximately four times that of CBD. This particular formulation is applicable for several proven treatments, including, but not limited to severe pain from arthritis or cancer.

It should be noted that while one specific example of a THC Rich compound or formula is depicted and described in FIG. 7, the invention is not intended to be limited thereto as other ranges and terpenes can be included. For example, one desired embodiment includes the actual amounts 700 as depicted in the left-side of the table, while various ranges 702 in accordance with the present invention are presented on the right-side of the table. Thus, in one embodiment, the THC Rich formulation includes the ranges 702 as depicted, while in other embodiments the ranges are decremented by a percentage point from each outer bound of the range until reaching the actual amounts 700, or any combination thereof. Further, the terpenes forming the composition can be any one or more of the listed terpenes as depicted, or any combination thereof, to total the amount of terpenoids present in the CTS. In some aspects, the terpenoids include approximately equal amounts of each of the different terpenes listed to comprise the total amount of terpenoids present; while in other aspects, one or more of the individual terpenes are presented in greater amounts than the other terpenes. As a non-limiting example, in one desired aspect or embodiment, all of the terpenes as listed in the figure are included, with a total percentage of Beta-Myrcene being approximately twice as much as that of the other terpenes.

As shown in FIG. 8, another desired embodiment according to the principles of the present invention is a THC Dominant compound. In this aspect, the formulation includes a considerably greater amount of THC than CBD, such that amount of TBD within the CTS is approximately twenty times that of CBD. This particular formulation is applicable for several proven treatments, including, but not limited to appetite stimulation. Unlike the results reported from studies in humans, appetite stimulation has not been effectively shown with animals. Surprisingly, the THC dominant formula did result in appetite stimulation.

It should be noted that while one specific example of a THC Dominant compound or formula is depicted and described in FIG. 8, the invention is not intended to be limited thereto as other ranges and terpenes can be included. For example, one desired embodiment includes the actual amounts 800 as depicted in the left-side of the table, while various ranges 802 in accordance with the present invention are presented on the right-side of the table. Thus, in one embodiment, the THC dominant formulation includes the ranges 802 as depicted, while in other embodiments the ranges are decremented by a percentage point from each outer bound of the range until reaching the actual amounts 800, or any combination thereof. Further, the terpenes forming the composition can be any one or more of the listed terpenes as depicted, or any combination thereof, to total the amount of terpenoids present in the CTS. In a desired aspect or embodiment, the terpenoids include approximately equal amounts of each of the different terpenes listed in FIG.

8 to comprise the total amount of terpenoids present; while in other aspects, one or more of the individual terpenes are presented in greater amounts than the other terpenes.

As can be appreciated by those skilled in the art, there are several variations that are envisioned to be within the scope of the present application, as well as several therapeutic advantages to the invention described herein. Several additional non-limiting examples are provided below.

The present disclosure further relates to the use of a solution containing Cannabidiol (CBD), Tetrahydrocannabinol (THC) and Terpenes for the reduction of total convulsive seizure frequency in the treatment of idiopathic epilepsy in non-human mammals. The disclosure further relates to the use of the CTS in combination with one or more anti-epileptic drugs (AEDs).

In certain preferred embodiments, the cannabinoid drug mixture concentrate includes from about THC 5% (or between 0.001%-20%) THC, CBD 5% (or between 0.001%-20%) cannabidiol, from about 0 to about 25% of each, CBDA, CBDV, CBG, CBC and other cannabinoids for a total cannabinoid level of from other cannabinoids 3% (or between 0.001%-15%), terpene(s) 3% (or between 0.001%-18%) terpenes (derived from *cannabis* or other plant or synthetically made), including but not limited to Pinene, Myrcene, Limonene, Beta-Caryophyllene, Linalool, Alpha Humulene. In certain desired embodiments, the cannabinoid drug mixture includes CBD and less than 0.3% of THC, along with terpenes, additional cannabinoids and a lipophilic carrier (excipient) such as MCT oil or any other binder (carrier) as known by those skilled in the art, that may be required to bind the CBD and THC into a suitable form for the use in oral delivery.

In other aspects, the formula includes:
1. CDB approximately 5% (or between 0.001%-20%)
2. THC approximately 5% (or between 0.001%-20%)
3. Terpene(s) approximately 3% (or between 0.001%-25%)
4. Other cannabinoids approximately 3% (or between 0.001%-15%)
5. An excipient, such as a lipophilic carrier (e.g., MCT Oil approximately 65% (or between 60%-99.99%)).

In certain desired embodiments the cannabinoids are formulated into CBD to THC ratios, several non-limiting examples of which are as follows: CBD (> 0.3% THC), 30:1, 20:1, 10:1, 4:1, 3:1, 1:1; 1:3, 1:4, 1:10, 1:20, 1:30. As noted above, the remaining components in addition to the CBD and THC (per the ratios) are selected based on the specific delivery method as selected and/or formulated. It should also be noted that the various terpenes as included are also active ingredients for the reasons stated therein.

The compositions of the present invention are in a desired embodiment transmucosal solutions, and are formulated for oromucosal administration. The transmucosal absorption rate of CTS through the oral mucosa is increased by increasing the contact surface of the oral mucosa with the compositions. Therefore, the transmucosal compositions of this invention should desirably be administered directly to the surface of the oral mucosa.

The invention is also directed to a topical formulation, comprising a cannabinoid drug in a formulation suitable for administration. The topical formulation may be prepared as an immediate, controlled or sustained release formulation.

The drug formulations useful in the present invention may be in a form selected from a topical formulation (e.g, a mousse, cream, ointment or gel); a transdermal device; an orally administered liquid or solid, a liquid or solid delivered through mucous surfaces or an implantable or injectable formulation.

In certain desired embodiments, the cannabinoid drug(s) is also administered to the mammal at or in proximity to an injured area on the mammal. For example, if the four-legged mammal has an injury to its leg, the cannabinoid drug(s) may also be administered to the leg or hip area. If the four-legged mammal has an injury to its hip, the cannabinoid drug(s) may also be administered directly to the hip region. In one embodiment, the CTS can be used as a topical treatment, combined with an oromucosal treatment for acute injury or localized rash or injured skin area.

In other embodiments, the cannabinoid drug is administered via implantation or injection. In such embodiments, the therapy is accomplished via the availability of the drug(s) at the free nerve endings under the epidermis. In such embodiments, the drug may be incorporated into an implantation device or may be incorporated into a carrier such as a gel or matrix that will provide a prolonged release/effect of the cannabinoid drug(s) at the site. The carrier may be a hydrophilic or hydrophobic material, a colloidal material, and may be in a state ranging from a viscous liquid to a solid polymeric insert.

Certain embodiments of the invention are directed to a method of treatment, comprising delivering a cannabinoid drug(s) by application as a cream/gel or a sustained release patch, or through any other suitable delivery method or technique.

Also as can be appreciated by those skilled in the art, the CTS as described herein can be made using any suitable technique or process, several non-limiting examples of which are provided below. A process for the isolation and purification of cannabinoids from *cannabis* plant material of different varieties comprising the following steps: a) extracting the plant material using optionally an organic solvent of supercritical fluid with or without modifier followed by evaporation of the extraction solvent to yield crude extract; b) optionally winterizing the crude extract prior to derivatization to remove hydrocarbons and waxes and derivatizing the crude extract, or optionally thin film distilled extract with a t-boc-amino acid to convert cannabinoids to their t-boc-amino acid esters; c) purifying the derivatized extract using normal phase column chromatography to isolate individual esters of different cannabinoids; d) base hydrolyzing the isolated individual cannabinoid ester to regenerate the free cannabinoid with high purity (>90% pure-100% pure); and e) optionally re-chromatographing the isolated cannabinoids to increase purity to a desired level.

The following describes the production of the highly-purified (>90% w/w) THC extract which has a known and constant composition.

In one example, the drug substance is a liquid butane extract of high-THCA containing chemotypes of *Cannabis sativa* L. which had been further purified by a solvent crystallization method to yield THC. The crystallization process specifically removes other cannabinoids and plant components to yield greater than 90% THC.

The *Cannabis* sativa L. plants are grown, harvested, and processed to produce a botanical extract (intermediate) and then purified by crystallization to yield the THC (drug substance).

The plant starting material is referred to as Botanical Raw Material (BRM); the botanical extract is the intermediate; and the active pharmaceutical ingredient (API) is THC, the drug substance.

The purity of the THC drug substance achieved is greater than 90%. The possible impurities are related cannabinoids THCV, CBDA, CBDV, CBG, CBC and CBD.

Both the botanical starting material and the botanical extract are controlled and tested for purity and consistency.

Production of the intermediate: An overview of the steps to produce a botanical extract, the intermediate, are as follows:
1. Growing
2. Extraction No. 1 - using liquid Butane
3. Extraction No. 2 - 'winterization' using ethanol
4. Filtration
5. Evaporation High THC chemovars were grown, harvested and dried and stored in a dry room until required. The botanical raw material (BRM) was finely chopped. The milled BRM was stored in a freezer for up to 3 months prior to extraction.

Extraction No. 1 was performed using liquid butane to produce botanical drug substance (BDS) which was used to produce the test material.

The crude THC BDS was winterized in Extraction No. 2 under standard conditions. The precipitated waxes were removed by filtration and the solvent evaporated using the rotary evaporator (water bath up to 140° F.) to yield the BDS.

Preparation of Highly Purified CBD Extract: The following describes the production of the highly-purified (>90% w/w) CBD extract which has a known and constant composition which was used for the expanded access trials described in Examples below.

In one example, the drug substance is a liquid butane extract of high-CBDA containing chemotypes of Cannabis sativa L. which had been further purified by a solvent crystallization method to yield CBD. The crystallization process specifically removes other cannabinoids and plant components to yield greater than 90% CBD.

The Cannabis sativa L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

The purity of the CBD drug substance achieved is greater than 90%. The possible impurities are related cannabinoids CBDA, CBDV, CBG, and CBC, THC and THCV.

Production of the Intermediate: An overview of the steps to produce a botanical extract, the intermediate, are as follows:
1. Growing
2. Extraction No. 1- using liquid Butane
3. Extraction No. 2 - 'winterization' using ethanol
4. Filtration
5. Evaporation High CBD chemovars were grown, harvested and dried and stored in a dry room until required. The botanical raw material (BRM) was finely chopped. The milled BRM was stored in a freezer for up to 3 months prior to extraction.

Extraction No. 1 was performed using liquid butane to produce botanical drug substance (BDS) which was used to produce the test material.

The crude CBD BDS was winterized in Extraction No. 2 under standard conditions. The precipitated waxes were removed by filtration and the solvent evaporated using the rotary evaporator (water bath up to 140° F.) to yield the BDS.

Preparation of Terpene Extracts: The traditional methods of terpene extraction is steam distilling and hydro-distillation. Steam distilling involves suspending a basket of herb above a vessel of boiling water. The steam passes through the perforated basket and penetrates the plant material. Only lighter oils such as monoterpenes are soluble in the steam. As the terpene-entrained steam passes out of the top of the distiller it comes in contact with a cooled condenser which liquefies the water and oils. The lighter oils float on the surface of the water and are easily collected. There is usually a water soluble fraction of oil that stays dissolved and gives the water a milky look. This is called hydrosol. Hydro-distillation is similar to steam distilling except that the herb is placed directly in the boiling water.

The main downside to these methods is the extreme heat involved. Boiling water is accomplished at 212° F.). Many plant compounds are altered or destroyed at these temperatures. This means the medicinal quality of the oil extract is compromised. Thus, the preferred method of extraction is under low temperature in a vacuum steam distiller. Supercritical CO2 extraction is another method of extraction whereby extracts of different molecular weight will drop out at different times or into different separation chambers.

Yet another example of manufacturing steps to produce the drug substance from the intermediate botanical extract are as follows:
1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30-liter stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 140° F. until dry before submitting the drug substance for analysis.

The dried product was stored in a freezer at minus 4° F. in a pharmaceutical grade stainless steel container, with FDA food grade approved silicone seal and clamps.

The therapeutically active agents used in the formulations and methods of the invention comprise cannabinoid drug(s). Cannabinoids are a diverse class of chemical compounds that act on cannabinoid receptors on cells and influence neurotransmitter release in brain. These receptor proteins include endocannabinoids produced naturally in humans and animals, phytocannabinoids in cannabis and some other plants, and chemically manufactured synthetic cannabinoids. Endo, phyto and/or synthetic cannabinoids cause neurotransmitter release which results in nerve transmission. Phytocannabinoid DELTA 9-tetrahydrocannabinol (THC), is primary psychoactive compound of cannabis. Cannabidiol (CBD) is another major constituent of the plant, up to 40% extracts of plant resin. Cannabidiol (CBD) is one of many active cannabinoids in cannabis. The cannabinoid may be derived from endocannabinoids (derived, e.g., from foods (Omega-3s and Omega-6s); phytocannabinoids (plant derived, e.g., from buds, tinctures, extracts, including tetrahydrocannabinol (THC), cannabidiol (CBD), cannabinol (CBN), etc.); and synthetic cannabinoids (such as tetrahydrocannabinol (THC)). At least 85 different cannabinoids isolated from *cannabis* exhibit varied effects. In certain desired embodiments, the cannabinoid drug(s), or are not psychoactive or are substantially not psychoactive (meaning that if included in the formulation, they are not in sufficient amount that a unit dose of the formulation would cause the patient to have a psychoactive effect). In certain desired embodiments, as will be explained further below, the cannabinoid drug is actually a mixture of two or more cannabinoids (e.g., CBD and THC together in a CBD:THC ratio that provides a therapeutic effect while substantially not psychoactive or not psychoactive at all).

The endocannabinoid system ("ECS") consists of a group of endogenous cannabinoid receptors located in mammalian brain and throughout the central and peripheral nervous systems. These entail neuromodulatory lipids and their associated receptors. As the body's "endogenous," cannabinoid system, ECS is involved in a variety of physiological processes including neurological functions dealing with pain, mood, memory; and, movement, and sensation. The body's immune function and cell homeostasis is also maintained by ECS. It mediates the psychoactive effects of the *cannabis* (marijuana) plant. Cannabinoids are a diverse class of compounds that include many of the unique compounds found in marijuana.

Cannabinoids produce physiological and behavioral effects through interaction with specific membrane-bound receptors. Two primary endocannabinoid receptors have been identified in humans: CB1 and CB2. There is mounting evidence that more endocannabinoid receptors exist. CB1 receptors are found predominantly in brain (specifically in basal ganglia and limbic system, including hippocampus) and nervous system, as well as in peripheral organs and tissues. These are acted on by the endocannabinoid binding molecule Anandamide. Of G protein-coupled type receptors (GPCR) in human brain, cannabinoid receptors are the most plentiful. CB1 receptors responsible for euphoric and anticonvulsive effects of *cannabis*. CB2 receptors found only in peripheral nervous system appear responsible for anti-inflammatory effect such as pain relief. One other main endocannabinoid is 2-Arachidonoylglycerol (2-AG), active at both CB1 and CB2 cannabinoid receptors. Its mimetic phytocannabinoid is cannabidiol (CBD), while that of Anandamide is THC, responsible for psychoactive effects. 2-AG and CBD are involved in regulation of appetite, immune system functions and pain management.

Tetrahydrocannabinol (THC) has been the primary focus of *cannabis* research since 1964, when Raphael Mechoulam isolated and synthesized it. More recently, the synergistic contributions of cannabidiol to *cannabis* pharmacology and analgesia have been scientifically demonstrated. Other phytocannabinoids, including tetrahydrocannabivarin, cannabigerol and cannabichromene, exert additional effects of therapeutic interest. Innovative conventional plant breeding has yieldedc *cannabis* chemotypes expressing high titres of each component for future study.

CBD is considered the "medical component" of *cannabis* and hemp. CBD is considered to have a wide scope of medical applications. CBD acts as 5-HT1A receptor agonist which may explain its antidepressant, anxiolytic, and neuroprotective effects. Cannabidiol modulates opioid receptors involved with pain perception. CBD is not psychoactive and relieves convulsion, inflammation, anxiety, and nausea. It has also been found to play a role in preventing short-term memory loss from THC. Antipsychotic effects of cannabidiol represent potential treatment of schizophrenia. Oral CBD formulation received orphan drug status in US as treatment for Dravet syndrome, an intractable seizure disorder also known as Severe Myoclonic Epilepsy of Infancy (SMEI). Nabiximols, trade name Sativex, is an aerosolized mist for oral administration containing 1:1 ratio of CBD and THC approved 2005 in Canada for multiple sclerosis associated pain. CBD has a greater affinity for CB2 than CB1 receptor.

CBD acts as serotonin (5-HT1A) receptor agonist which may explain its antidepressant, anxiolytic, and neuroprotective effects. CBD modulates opioid receptors involved with pain perception. CBD is not psychoactive and relieves convulsion (seizures), inflammation, anxiety, and nausea. It has been found to play a role in preventing short-term memory loss from THC. Antipsychotic effects of cannabidiol represents potential treatment of schizophrenia. CBD has a greater affinity for CB2 than CB1 receptors.

*Cannabis* terpenoids (e.g., limonene, myrcene, alpha-pinene, linalool, beta-caryophyllene, caryophyllene oxide, nerolidol and phytol) share a precursor with phytocannabinoids, and are all 18quale and fragrance components common to human diets that have been designated Generally Recognized as Safe by the US Food and Drug Administration and other regulatory agencies. Terpenes are quite potent, and affect animal and even human 18qualene when inhaled from ambient air at serum levels in the single digits ngM1-1. They display unique therapeutic effects that may contribute meaningfully to the entourage effects of *cannabis*-based medicinal extracts. Thus, in certain embodiments, the formulations and treatments of the present invention include an active drug component which comprises both a phytocannabinoid(s) and a terpene(s). Phytocannabinoid-terpenoid interactions may produce synergy with respect to treatment of pain, inflammation, depression, anxiety, addiction, epilepsy, cancer, fungal and bacterial infections (including methicillin-resistant Staphylococcus aureus).

It is known to those skilled in the art that studies have suggested that many cannabinoid compounds work with one another and together with terpenoids synergistically to produce what is known as the "entourage effect." Thus, in certain desired embodiments, the formulations of the invention contain more than one cannabinoid compound along with one or more terpenoids, which provide an "entourage effect."

CBD has anti-psychotic effects which may counteract psychotomimetic effects of THC, euphoric and hallucinogenic component of *cannabis*. Reports show CBD safe and well-tolerated alternative treatment for schizophrenia. A double blind trial comparing purified cannabidiol to atypical antipsychotic amisulpride in acute paranoid schizophrenia showed both treatments were associated with significant decrease in psychotic symptoms after 2 weeks; but cannabidiol was associated with significantly fewer side effects. Studies show cannabidiol affects limbic system, decreasing symptoms of social anxiety and isolation. Cannabidiol has demonstrated antidepressant-like effects in animal models of depression.

In certain desired embodiments, the cannabinoid is not psychoactive, or only mildly psychoactive. CBD is not psychoactive, and therefore in certain desired embodiments, the active cannabinoid drug comprises cannabidiol, or consists essentially of cannabidiol, or consists of cannabidiol. In other desired embodiments, cannabidiol comprises from about 0.001% to about 99.9% of the total amount of cannabinoid drug(s) included in the formulations and treatments of the present invention. In other desired embodiments, cannabidiol comprises about 20%, about 30%, about 40%, about 50%, about 60%, about 70%, about 80%, about 90% or more, or greater than about 95% of the total amount of cannabinoid drug(s) included in the formulations and treatments of the present invention. In certain embodiments, the CBD is derived from crystalline powder, such that the powder is about 90% pure CBD or greater. In other desired embodiments, cannabidiol comprises at least about 20% of the total amount of cannabinoid drug(s) included in the formulations and treatments of the present invention. In other embodiments, the cannabinoid drug comprises cannabinol (which is only mildly psychoactive). In certain embodiments, the cannabinoid drug(s) contained in the formulations of the invention is hemp CBD. In other embodiments, the cannabinoid drug(s) is *cannabis*-based and comprises a THC-CBD (and optionally other cannabinoid combinations derived from *cannabis*). As CBD and THC have different mechanisms of action, they may act synergistically, e.g., to control seizures. In such embodiments, the therapeutic effect may be via the "entourage effect".

In other embodiments, the drug is a cannabinoid such as an endocannabinoid (derived, e.g., from foods (Omega-3s and Omega-6s); a phytocannabinoid (plant derived, e.g., from buds, tinctures, extracts, including tetrahydrocannabinol (THC), cannabidiol (CBD), cannabinol (CBN), etc.); and synthetic cannabinoids (such as tetrahydrocannabinol (THC)), mixtures thereof, and the like. Further representative cannabinoids useful in the present invention include cannabigerol (CBG), cannabichchromene (CBC), cannabicyclol (CBL), tetrahydrocannabivarin (THCV), cannabidivarin (CBDV), or a derivative of any of the foregoing. In certain embodiments, a synthetic cannabinoid is used. Synthetic cannabinoids encompass a variety of distinct chemical classes: the classical cannabinoids structurally related to THC, including the nonclassical cannabinoids (cannabimimetics) including the aminoalkylindoles, 1,5-diarylpyrazoles, qualene17p, and arylsulfonamides, as well as eicosanoids related to the endocannabinoids. Cannabigerol ("CBG") is non-psychotomimetic but still impacts the overall effects and affects of *cannabis*. CBG acts as a alpha2-adrenergic receptor agonist, 5-HT1A receptor antagonist, CB1 receptor antagonist, and also binds to the CB2 receptor. CBC is non-psychoactive, and exhibits anti-inflammatory and analgesic properties. Evidence suggests that CBC may play a role in anti-inflammatory and anti-viral effects, may have antidepressant effects, may promote neurogenesis, and may contribute to the overall analgesic effects of *cannabis*. Delta-9-tetrahydrocannabinol (Dronabinol; commercially available in the U.S. under the tradename Marinol) is used as an appetite stimulant, anti-emetic, and analgesic. Nabilone (Cesamet, Canemes), a synthetic cannabinoid and an analog of Marinol; Rimonabant (SR141716), a selective CB1 receptor inverse agonist once used as an anti-obesity drug under the tradename Acomplia, and was also used for smoking cessation.

In yet further embodiments, the cannabinoid drug(s) comprises a natural cannabinoid compound, a synthetic cannabinoid compound, a semi-synthetic cannabinoid compound, or mixtures thereof. Illustrative of such compounds are cannabinoids or cannabinoid analogues selected from the group consisting of cannabinol, cannabidiol, delta 9-tetrahydrocannabinol, delta 8-tetrahydrocannabinol, hydroxy-tetrahydrocannabinol, 11-hydroxy-9-tetrahydrocannabinol, levonantradol, delta 11-tetrahydrocannabinol, tetrahydrocannabivarin, dronabinol, amandamide, nabilone, a natural or synthetic analogue thereof, a natural or synthetic molecule with a basic cannabinoid structure, and mixtures of any of the foregoing. In certain embodiments, the cannabinoid drug(s) is industrial hemp or a non-psychoactive hemp product. In certain embodiments, the cannabinoid drug(s) included in the treatment and/or formulations of the present invention comprise a ligand that binds to the CB1 or the CB2 receptor.

In certain embodiments of the invention, the cannabinoid(s) is administered together with (e.g., in the same formulation), or simultaneously (but separately) or sequentially with an additional active agent(s) ("drug(s)") suitable for treating the patient's disease state or condition. Classes of drugs which would be suitable as an additional active agent(s) include, but are not limited to:

1. Anti-Epileptic drugs: Examples include Valproic acid (Depacon®/Depakot®e), Leviteracetem (Keppra®), Lamotrigene (Lamictal®), Topiramate (Topamax®), Pregabalin (Lyrica®), Gabapentin (Neurontin®), Carbamazepine (Tegretol®), Oxcarbazepine (Trileptal®), Phenobarbital and other barbiturates, Tiagabine (Gabatril®), Retigabine™ (Valeant Pharmaceuticals), Lacosamide® (Schwarz Biosciences), and Perampanel® (Eisai) are in development as anti-epileptics and neuromodulators for other associated neurological, pain, and psychiatric conditions.
2. Anxiolytic drugs: Benzodiazepines: Examples include lorazepam (Ativan®), diazepam (Valium®), clonazepam (Klonopin®), chlordiazepoxide (Librium®), and alprazolam (Xanax®)
3. Neuroleptics/Anti-Psychotic drugs: Examples include chlorpromazine (Thorazine®), haloperidol (Haldol®), risperidone (Risperdal@), olanzapine (Zyprexa®) and quetiapine (Seroquel®).
4. Analgesics/Anti-Inflammatory drugs: Examples include prednisone, solumedrol, and other steroids, naproxen, aspirin, acetaminophen, voltaren, ketoprofen, ibuprofen, other NSAID's.
5. Parkinson's Disease/Similar or Related Syndrome drugs: Examples include dopamine agonists such as apomorphine.
6. Dystonia (cervical and otherwise), which sometimes occur in conjunction with spasmodic torticollis and spastic conditions: Examples of drugs include dopamine agonists such as apomorphine.
7. Benign essential/familial tremor, tremor related to MS, chronic encepahalopathies such as from stroke or head injuries, congenital CNS degeneration conditions/cerebral palsy, cerebellar degeneration syndromes, and spasticity conditions from the above: Examples of drugs include dopamine agonists such as apomorphine.
8. Neuropathic/Neurogenic pain drugs: Examples include carbamazepine, gabapentin, topiramate, zonisamide, phenytoin, desipramine, amitriptyline, imipramine, doxepin, protriptyline, pentoxifylline, and hydroxyzine.
9. Smoking Cessation drugs: Examples include drugs such as varenicline.
10. Appetite Suppressant drugs: Examples include drugs such as Sibutramine.
11. Neurodegenerative Diseases: Examples include drugs such as Aricept/donepezil, Exelon/rivastigmine, Reminyl/Razadyne/galantamine, and Namenda/memantine and their naturally occurring counterparts, as well as NMDA antagonists.
12. Multiple Sclerosis (MS): Examples include drugs such as 4-aminopyridine.
13. Insomnia: Examples include drugs such as zolpidem
14. Fatigue: Examples include drugs such as pemoline and Modafinil.

15. Vertigo, Nausea and/or Dizziness: Examples include drugs such as as meclizine, dimenhydrinate, prochlorperazine, scopolamine and diphenhydramine.
16. Writer's cramp and restless leg syndrome: Examples include dopamine agonists such as apomorphine.

In certain embodiments, the additional drug(s) includes a dopamine agonist such as apomorphine (Apokyn®, APOgo®), pramipexole (Mirapexin®), ropinirole (Requip®), bromocriptine (Parlodel®), cabergoline (Cabaser®, Dostinex®), pergolide (Permax®, Celance®) rotigotine (Neupro®), mixtures of any of the foregoing, or other dopamine agonists known to those skilled in the art One skilled in the art will appreciate that dopamine agonists other than apomorphine may be used in the formulations and methods of the present invention, and all such agents are meant to be encompassed by the term "dopamine agonists" For example, such drugs include, but are not limited to, carbidopa (Sinemet®), dopamine agonists (Requip®, Rotigotine®, Mirapex®), COMT inhibitors (Entacapone®, Tocapone), rasagiline (Azilect®) (MAO inhibitors) and MAO-B inhibitors (Selegiline (Eldepryl®).

In other embodiments, the additional drug(s) includes an opioid such as morphine, codeine, dihydrocodeine, hydrocodone, hydromorphone, nicomorphine, oxycodone, oxymorphone, fentanyl, alphamethylfentanyl, alfentanil, sufentanil, remifentanil, carfentanyl, ohmefentanyl, thebaine, oripavine, diacetylmorphine (heroin), phenylpiperidines such as pethidine (meperidine) and ketobemidone, allylprodine, prodine, propoxyphene, dextropropoxyphene, dextromoramide, bezitramide, piritramide, methadone, dipipanone, levomethadyl Acetate (LAAM), loperamide, diphenoxylate, dezocine, pentazocine, phenazocine, buprenorphine, dihydroetorphine, etorphine, butorphanol, nalbuphine, levorphanol, levomethorphan, lefetamine, meptazinol, tilidine, tramadol, tapentadol, mixtures thereof, and the like.

In yet other embodiments, the additional drug(s) is tarpentadol (a centrally acting oral analgesic having two mechanisms of action combining mu-opioid receptor agonism and norepinephrine reuptake inhibition).

In yet other embodiments, the additional drug(s) is a selective norepinephrine reuptake inhibitor, such as Atomoxetine (Strattera®), Mazindol (Mazanor®, Sanorex®), Nisoxetine (LY-94939), Reboxetine (Edronax®, Vestra®), Viloxazine (Vivalan®), mixtures thereof, and the like.

In yet other embodiments, the additional drug(s) is a benzodiazepine, such as lorazepam (Ativan®), diazepam (Valium®), clonazepam (Klonopin®), chlordiazepoxide (Librium®), alprazolam (Xanax®), temazepam (Restoril®), mixtures thereof, and the like. In other embodiments, the drug is a neuroleptic or psychotropic such as chlorpromazine (Thorazine®), haloperidol (Haldol®), risperidone (Risperdal®), olanzapine (Zyprexa®) and quetiapine (Seroque®).

In other embodiments, the additional drug(s) is an agent that treats depression and/or anxiety, for example, selective serotonin reuptake inhibitors (SSRIs) such as fluoxetine (Prozac), sertraline (Zoloft®), venlafaxine (Effexor®), citalopram (Celexa®), parocetine (Paxil), mixtures thereof, and the like (such as trazodone (Desyrel)), and/or serotonin-norepinephrine reuptake inhibitors (SNRI), such as Desvenlafaxine (Pristiq®), Duloxetine (Cymbalta®), Milnacipran (Ixel®, Savella®), Venlafaxine (Effexor®), mixtures thereof, and the like.

In yet other embodiments, the additional drug(s) is a norepinephrine-dopamine reuptake inhibitor (NDRI), such as Amineptine (Survector®), an aminoketone antidepressant such as Bupropion (Wellbutrin®, Zyban®), Dexmethylphenidate (Focalin), Methylphenidate (Ritalin®, Concerta®), Nomifensine (Merital®), a phenylpiperazine antidepressant such as nefazodone (Serzone®), a piperazino-azepine antidepressant such as mirtazapine (Remeron®), mixtures thereof, and the like.

In yet other embodiments, the additional drug(s) may be an NMDA receptor antagonist. Phencyclidine, ketamine, and dextromethorphan, are used as recreational drugs. At subanesthetic doses, however, these drugs have mild stimulant effects, and these agents have shown promise for the treatment of conditions that involve excitotoxicity, including traumatic brain injury, stroke, and neurodegenerative diseases such as Alzheimer's, Parkinson's, and Huntington's.

Additionally, the additional drug(s) may be an agent that treats neuropathic/neurogenic pain (pain that arises from nerve dysfunction and not as a result of injury, e.g., trigeminal neuralgia), such as carbamazepine, gabapentin, topiramate, zonisamide, phenytoin, desipramine, amitriptyline, imipramine, doxepin, protriptyline, pentoxifylline, and hydroxyzine.

In other embodiments, the additional drug(s) treats insomnia, such as zolpidem (Ambien®).

In other embodiments, the additional drug(s) treats fatigue. Such drugs include central nervous system stimulants such as pemoline (Cylert®) and Modafinil (Provigil®).

In yet other embodiments, the additional drug(s) treats vertigo, nausea and/or dizziness, such as meclizine (Antivert®), dimenhydrinate (32qualene32), prochlorperazine (32qualene32®), scopolamine (Transderm®) and diphenhydramine (Benadryl®).

In yet other embodiments, the drug is a serotonin-norepinephrine reuptake inhibitor (SNRI), such as Desvenlafaxine (Pristiq®), Duloxetine (Cymbalta®), Milnacipran (Ixel®, Savella®), Venlafaxine (Effexor®), mixtures thereof, and the like.

In yet other embodiments, the additional drug(s) is a tricyclic antidepressant (TCA), such as Amitriptyline (Elavil®), Butriptyline (Evadene®, Evadyn®e), Clomipramine (Anafranil®), Desipramine (Norpramin®, Pertofrane), Dosulepin (Prothiade), Doxepin (Adapin, Sinequan), Imipramine (Tofranil®), Lofepramine (Feprapax®, Gamanil®, Lomont®), Nortriptyline (Aventyl®, Nortrilen®, Pamelor®), Protriptyline (Vivacti®1), Trimipramine (Surmontil®), mixtures thereof, and the like.

In yet other embodiments, the additional drug(s) is a tetracyclic antidepressant, such as Amoxapine (Asendin®), Maprotiline (Ludiomil®), Mianserin (Tolvon®), mixtures thereof, and the like.

In yet other embodiments, the additional drug(s) is an atypical antipsychotic, such as Ziprasidone (Geodon®, Zeldox®), Nefazodone (Serzone®), and the like.

In yet other embodiments, the additional drug(s) is an anti-convulsant or anti-epileptic drug such as arylsulfonimide analogues such as Acetazolimide (Diamox)®, tricyclic iminostilbene derivatives such as carbamazepine (Tegreto®), benzodiazepines such as clonazepam (Klonopin®), clorazepate dipotassium (Tranxene®), lorazepam (Ativan®) and diazepam (Valium®), carboxylic acid derivatives such as valproic acid (Depakene®) and divalproex sodium (Depakote®), succinimide derivatives such as ethosuximide (Zarontin®), carbamate esters of 2-phenyl-1,3-propanediol such as felbamate (Felbatol®), hydantoins such as phenytoin (Dilantin®), phenytoin sodium (Dilantin®) and fosphenytoin sodium (Cerebyx®), structural analogues of GABA such as gabapentin (Neurontin®) and pregabalin (Lyrica®), phenyltriazines such as lamotrigine (Lamictal®), pyrrolidine derivatives such as levitiracetam (Keppra®), tricyclic iminostilbene derivatives such as 33qualene33pine (Trileptal), barbiturates such as Phenobarbital, desoxybarbiturates such as primidone (Mysoline®), nipecotic acid derivatives such as tiagabine hydrochloride (Gabitril®), sulfamated monosaccharides such as topiramate (Topamax®), oxazolidinedione derivatives such as trimethadione (Tridione®), and methanesulfonamides such as zonisamide (Zonigran®). Additional drugs such as Retigabine® (Valeant Pharmaceuticals), Lacosamide® (Schwarz Biosciences), and Perampanel® (Eisai) are in development as anti-epileptics and neuromodulators for other associated neurological, pain, and psychiatric conditions, and thus are further examples of potentially useful drugs in the present invention.

In yet other embodiments, the additional drug(s) is an analgesic/anti-inflammatory agent such as acetaminophen, prednisone, solumedrol, and other steroids; naproxen, aspirin, voltaren, ketoprofen, ibuprofen, nabumetone, and other NSAID's The NSAID may be COX-1, COX-2 or mixed COX-1/COX-2 inhibitors Examples of COX-2 inhibitors include oxicam, meloxicam, and the more selective celecoxib, rofecoxib, valdecoxib, parecoxib and etoricoxib. Further examples of corticosteroids include methylprednisolone, prednisolone, dexamethasone, and adreno-corticotrophic hormone (ACTH), corticotropin.

Additionally, the additional drug(s) may be an agent that treats neuropathic/neurogenic pain (pain that arises from nerve dysfunction and not as a result of injury, e.g., trigeminal neuralgia), such as carbamazepine, gabapentin, topiramate, zonisamide, phenytoin, desipramine, amitriptyline, imipramine, doxepin, protriptyline, pentoxifylline, and hydroxyzine, mixtures thereof, and the like.

In other embodiments, the additional drug(s) is 4-aminopyridine (4-AP; also known as Fampridine®) or a pharmaceutically acceptable derivative thereof. This drug has been shown to have the ability to improve the communication between damaged nerves, which may result in increased neurological function in the treatment of conditions such as multiple sclerosis (MS). An example of another such drug is 3,4 diaminopyridine.

In other embodiments, the additional drug(s) is useful for the treatment of Dementia/Alzheimer's disease, such as Aricept®/donepezil, Exelon®/rivastigmine, Reminyl®/Razadyne®/galantamine, and Namenda®/memantine, their naturally occurring counterparts, and mixtures thereof.

In certain desired embodiment, the CTS drug(s) are incorporated into a pharmaceutically acceptable oral liquid or gel formulation for oromucosal delivery.

In yet another embodiment, the CTS can be incorporated into a self-emulsifying drug delivery systems (SEDDS) or self-micro-emulsifying drug delivery systems (SMEDDS), which are isotropic mixtures of oils, surfactants, solvents and co-solvents/surfactants. The SEDDS or SMEDDS format are a suitable solution to improving oral drug delivery of poorly soluble and low permeability drugs.

In yet another embodiment, the CTS can be incorporated into a modelling and experiments in drug delivery systems (MEDDS). These systems combine a platform or carrier with a drug in such a way that the drug is efficiently released to a target tissue or organ, while maintaining the drug concentration within a therapeutic window.

In yet another embodiment, the CTS can be incorporated into a nano-drug delivery system. Nano-drug delivery systems (NDDSs) are a class of nanomaterials that have abilities to increase the stability and water solubility of drugs, prolong the cycle time, increase the uptake rate of target cells or tissues, and reduce enzyme degradation, thereby improve the safety and effectiveness of drugs.

In certain embodiments, the CTS drug(s) are incorporated into a pharmaceutically acceptable solid formulation such as a tablet, capsule for oral delivery.

In certain embodiments, the CTS drug(s) are incorporated into a pharmaceutically acceptable solid formulation such as a suppository.

In certain embodiments, the CTS drug(s) are incorporated into a pharmaceutically acceptable solid for a transdermal patch.

In certain embodiments, the CTS drug(s) are incorporated into a pharmaceutically acceptable liquid form for an injectable.

In certain embodiments, the CTS drug(s) are incorporated into a pharmaceutically acceptable liquid form for a mist.

In certain embodiments, the CTS drug(s) are incorporated into a pharmaceutically acceptable solid for powder.

In certain embodiments, the CTS drug(s) are manufactured using 3DP, a form of "additive manufacturing," wherein a structure is built by depositing or binding required materials in successive layers to produce a three-dimensional (3D) object, including rapid prototyping, solid freeform fabrication and additive manufacturing.

In yet other embodiments, the CTS drug(s) can be formed as nano-drugs, nano-encapsulated drugs, glycosides, synthetics and analogs – prodrugs (e.g., THC glycosides via prodrugs), and/or formulated as a spray, mist, or vapor for delivery.

In yet other embodiments, the CTS is nano-emulsified (water compatible) and water soluble. For example, glycosylation is the process of attaching a sugar molecule to the cannabinoid, which makes it water soluble (rather than just water "compatible" or both water soluble and water compatible). In yet other embodiments, the CTS is formed as cannabinoid glycoside prodrugs and methods of synthesis.

In other embodiments, the CTS is formulated to provide for immediate release. Alternatively, in yet other embodiments, the CTS is formulated for a controlled or sustained release.

In other embodiments, the CTS is provided as an additive to animal food or feed. In other embodiments, the CTS includes a penetration or permeation enhancement (e.g. ethosomes).

In yet other embodiments, the CTS can be formulated as a liquid and administered as an intravenous (IV) treatment.

In yet other embodiments, the CTS can be formulated to include the necessary components to allow for the CTS to be administered as a powdered-metered-dose inhaler.

In yet other embodiments, the CTS can be added to a vaccine or taken with a vaccine (e.g., nasal mucosal administration), or as an additive to cattle feed or other animal feed. For example, in one embodiment, in the cattle feed, the CTS can be hemp-based CBD with less than 0.3% THC.

In yet other embodiments, the CTS can be formulated to provide for administration via trans-mucosal including nasal and cat ear (for example).

In yet other embodiments, the CTS can be formulated to include a numbing component (for dental procedure/dental cleaning). For example, the CTS in this aspect can be rubbed onto the gums.

In yet other embodiments, the CTS can be formulated to be provided as a gel or concentrated oil.

In yet other embodiments, the CTS can be formulated to be administered as both a nasal spray or solution and for transdermal application (or oromucosal and transdermal), for a way to control both chronic and acute breakthrough pain, as with cancer. In other aspects, a transdermal patch can be applied for (delayed) delivery and the oromucosal dose can be delivered immediately for breakthrough pain.

In yet other embodiments, the CTS can be formulated as a surfactant-based delivery systems, which includes microspheres, nanosized drug carriers (nanoparticles, nano-emulsions, stealth liposomes, nanogels, polymer-drug conjugates), novel powders, hydrogels and/or mixed micellar systems intended for systemic and/or localized delivery, or any combination thereof.

In certain embodiments, the pharmaceutically acceptable topical formulation of the CTS comprises a topical aqueous-based carrier, with an optional penetration enhancer. In certain desired embodiments, the topical aqueous-based carrier is a mousse, gel, or cream, and most preferably a mousse.

In certain desired embodiments, the mammal is a canine. In other desired embodiments, the mammal is a feline. In other desired embodiments, the mammal is a horse or other equine, or cattle, or any other farm animal or zoo animal. In other embodiments, the mammal is a goat, sheep, lamb, pig, wolf, cattle, etc. In yet other embodiments, the mammal is a monkey or other hominid.

In certain desired embodiments, the CTS is formulated in a pharmaceutically acceptable (immediate release) carrier, which includes the appropriate excipients to allow for such an immediate release. In certain desired embodiments, the CTS is formulated to be provided as a topical solution that is aqueous based, such as a cream or gel or mousse.

Thus, as can be appreciated, there are many variations of the CTS in accordance with the principles of the present invention and the active and inactive ingredients can be modified using any of the components as described herein, or any combination thereof, to provide the delivery and/or effect as described in the present disclosure.

(B) Method for Treating a Variety of Diseases and Disorders Using the Compound

The unique varieties of CTS as described herein have been shown in experimental results to be extraordinarily/unexpectedly effective in treating a variety of diseases and disorders, several examples of which are described throughout this disclosure. In terms of patient-specific, formulations were created specifically targeting animal receptors-specific terpenes added to aid in mitigation of THC (to avoid static ataxia), for example, and formulations were created specifically to treat certain conditions. While three specific examples are provided further below, it should be understood that the invention is not intended to be limited thereto as the CTS and various ratios of cannabinoids and terpenoids and dosages can be used to treat any number of ailments.

The endocannabinoid system (ECS) is involved in regulating a variety of physiological processes including appetite, pain and pleasure sensation, immune system, mood, and memory. Endocannabinoid receptors in the brain interact with cannabinoids from different sources, including (endocannabinoids (brain derived, e.g., from foods (Omega-3s and Omega-6s); phytocannabinoids (plant derived, e.g., from buds, tinctures, extracts, including tetrahydrocannabinol (THC), cannabidiol (CBD), cannabinol (CBN), etc.); and synthetic cannabinoids (such as tetrahydrocannabinol (THC)). Cannabinoids are a diverse class of chemical compounds that act on cannabinoid receptors on cells and influence neurotransmitter release in brain. These receptor proteins include endocannabinoids produced naturally in humans and animals, phytocannabinoids in *cannabis* and some other plants, and chemically manufactured synthetic cannabinoids. Phytocannabinoid .DELTA.9-tetrahydrocannabinol (THC) is the primary psychoactive compound of *cannabis*. Cannabidiol (CBD) is another major constituent of the plant, and comprises up to 40% extracts of plant resin. At least 85 different cannabinoids isolated from *cannabis* exhibit varied effects.

Benefits for treating symptoms of diverse neurologic and psychiatric conditions have been known and practiced by ancient civilizations for thousands of years, even resulting in recent patent issuances. By way of example, U.S. Pat. No. 6,630,507 is held by the United States Department of Health and Human Services, covering use of cannabinoids for treating a wide range of diseases. It is directed to a method of treating diseases caused by oxidative stress comprising administering a therapeutically effective amount of a cannabinoid (e.g., cannabidiol) that has substantially no binding to the NMDA receptor to a subject who has a disease caused by oxidative stress.

In certain desired embodiments, the disease or condition to be treated in the mammal includes degenerative myelopathy; Parkinson's disease; lameness and gait issues; elbow dysplasia; hip dysplasia; back and hind leg problems; arthritis; seizures; encephalopathy, including lethargy, focus/attentional problems, and cognitive issues: spasticity; epilepsy; cancer; glioblastoma; weakness; pain; numbness; anxiety and other mood disorders; hypertension; tremors; peripheral neuropathy; bowel and bladder control issues; inactivity; poor appetite; tumors (e.g., pituitary tumors); Cushing's disease; aggressive behavior; pruritus; dermatitis; anxiety: vomiting; lethargy; nausea: glaucoma, noise aversion; dystonia; personality change; restlessness, inflammatory bowel syndrome, neurological damage, as well as any other disease or condition in a mammal and a mammal other than humans that may be treated with a cannabinoid.

Thus, it is an object of the present invention to provide a method of treatment in mammals with administration of a composition consisting of one or more cannabinoids useful for the treatment of such diseases or conditions that may be treated via such therapy. As clearly understood by those skilled in the art, it should be noted that the inactive ingredients and various percentages as listed can be altered to include the relevant components as may be required according to the various delivery method. The specific inactive components as required by the various delivery methods are understood by those skilled in the art to accomplish a product or solution that is suitable per the listed or selected delivery method.

It is an object of the present invention to provide a method for the treatment of lameness and gait issues; behavioral problems, elbow dysplasia; hip dysplasia; back and hind leg problems; arthritis and other inflammatory diseases and inflammation-related pain; seizures and other disorders of the nervous system; encephalopathy, including lethargy, focus/attentional problems, and cognitive issues: spasticity; epilepsy; cancer; weakness; pain; numbness; anxiety and other mood disorders; hypertension; tremors; peripheral neuropathy; bowel and bladder control issues; inactivity; poor appetite; tumors (e.g., pituitary tumors); Cushing's disease; aggressive behavior; pruritus; dermatitis; skin disorders; vomiting; lethargy; nausea, glaucoma, noise sensitivity, noise phobias, chronic pain management; infections (bacterial, fungal, etc.); intervertebral disc disease (IVDD); kidney and liver disease; digestive tract upset; dystonia; personality change; as well as any other disease or condition in a mammal and a mammal other than human that may be treated with the CTS.

The invention is a solution and method for treating ailments in a mammal, including humans and mammals other than humans, companion animals, livestock, equine, zoo animals, poultry, cattle and fish by administering a CTS consisting essentially of tetrahydrocannabinol (THC); cannabidiol (CDB) (whole flower, hemp based, single molecule, distillate or isolate, natural or synthetic); other cannabinoids; *cannabis* terpenes; non-*cannabis* terpenes; and/or a lipophilic excipient or carrier such as MCT coconut oil.

In doing so, the solution and method can vary based on the particular ailment and administration method. For example, for the relief of seizures, the preferred solution contains a ratio of tetrahydrocannabinol (THC); cannabidiol (CDB); terpenes; other cannabinoids and an excipient such as MCT coconut oil or other binder (method of delivery). The various ratio or percentages (or any combination thereof) are described herein and illustrated in the figures. The resulting CTS can be delivered directly to the mouth in oil or gel using a highly graduated oral syringe, or dropper or by hand, for trans-mucosal absorption.

As noted above, the unique CTS(s) as described herein have been show in experimental results to be extraordinarily/unexpectedly effective in treating a variety of diseases and disorders, including at least (1) epilepsy, (2) anxiety, and (3) pain and inflammation. Each of these is described in further detail below.

(B) Treatment of Epilepsy

The present invention relates to the use of CTS therapy for the reduction of total convulsive seizure frequency in the treatment of idiopathic epilepsy in dogs. In this aspect, the CTS is desirably in the form of 4:1 CBD:THC ratio with at least one or more of the terpenes (or any combination thereof) as shown in FIG. 4.

In use, the CTS may be used concomitantly with one or more other anti-epileptic drugs (AEDs). Alternatively, the CTS may be formulated for administration separately, sequentially or simultaneously with one or more AEDs or the combination may be provided in a single dosage form. Where the CTS is formulated for administration separately, sequentially or simultaneously, it may be provided as a kit or together with instructions to administer the one or more components in the manner indicated.

Idiopathic epilepsy (IE) is the most common neurologic condition in dogs, affecting 0.5 to 5.7 percent of the pet dog population. IE is defined as reoccurring seizures with no identifiable structural cause. IE seizures typically occur between six months and six years of age; however, dogs outside this age range are more likely to have an underlying cause for their seizures, which is referred to as secondary epilepsy. In cats, the occurrence of IE is low (less than half a percent), and the onset of seizures typically happens between one and eight years of age.

A number of AEDs are licensed for the treatment of epilepsy in dogs. These include Phenobarbital, Potassium Bromide, Levetiracetam, Zonciamide and Gabapentin. Although a variety of drugs are used for management of epileptic dogs, there are no evidence-based guidelines regarding the choice of a first-line drug for long-term management of seizure control in dogs. In principle, administration of a single drug is preferred because it avoids drug interactions and it is more convenient for the owner. Phenobarbital and Potassium Bromide have been used as first-choice sole drugs as the standard of care for long-term treatment of epilepsy in dogs based on their long-standing history, widespread availability and low cost.

The most recent American College of Veterinary Internal Medicine consensus statement on seizure management in dogs indicates that anticonvulsant treatment should be initiated with phenobarbital or potassium bromide. However, a combination of Phenobarbital and Potassium Bromide is unsuccessful in controlling seizures in approximately 20% to 30% of dogs.

After initiation of a therapy, it is important to systematically monitor the seizure control, systemic effects of the drug, and drug concentrations in the blood. The focus of monitoring treatment is to optimize seizure control while minimizing adverse effects. Epilepsy management depends on accurate owner observation when assessing the efficacy of therapy. Owners need to maintain a log to document seizure occurrences and changes in medication administration. Adjustments in dosage often are based on the assessment of the seizure control in addition to blood drug concentration and drug side effects. It is important to have regular assessment of blood concentrations even at times when seizures are well controlled in order to monitor for toxic levels, especially for drugs with a greater potential for side effects (i.e. Phenobarbital and Potassium Bromide), to monitor for blood concentration fluctuations, and to have awareness when there is a need to make changes in therapy.

About 60-70 percent of epileptic dogs achieve good seizure control when their therapy is carefully monitored. Dogs that are not well controlled risk euthanasia due to poor quality of life for the dogs and their owners. Risk factors for euthanasia include younger age of onset, high initial seizure frequency, poor seizure control, and episodes of status epilepticus, or seizures that last longer than five minutes. Approximately 40-60 percent of dogs with epilepsy have one or more episodes of cluster seizures or status epilepsy, and a mean lifespan of only 8 years, compared to 11 years for those with epilepsy without episodes status epilepsy. Epileptic dogs that have had cluster seizures are known to be significantly less likely to achieve remission with any treatment. Though life expectancy of the pet may not be affected using currently existing treatment protocols, the odds of an epileptic going into complete remission and not requiring ongoing therapy are low: 6-8 percent in dogs. Thus, dogs with epilepsy usually require lifelong therapy and commitment from the pet owner. A balance between quality of life and therapeutic success is often key for an owner's commitment to their pet's therapy. The ineffectiveness and adverse effects of the commonly prescribed drugs require alternative treatment therapies, regardless of the pet owner's commitment.

Over the past forty years, there have been a number of animal studies on the use of the non-psychoactive CBD to treat seizures. For example, some studies determined that CBD was able to prevent seizures in mice after administration or pro-convulsant drugs or an electric current. However, these studies were conducted to determine toxicity in animals for the development of human medicine, rather than efficacy of the medicine in the treatment of animals.

In addition, McGrath, noting that THC is toxic for dogs, determined that high dosages of hemp CBD may be able to reduce seizure frequency in dogs. "Static ataxia," which is a unique neurological reaction to THC in canines, is explained by this high concentration of CB receptors in the cerebellum (see Literature Reference No. 22). Dogs in particular will suffer from "Static Ataxia" upon exposure to THC at doses >0.5 mg/kg IV (se Literature Reference No. 21). However, the high levels of CBD were also determined to cause ataxia in 2 of the 10 dogs from that study. Moreover, the CBD used was derived from hemp, containing less than 0.3% THC (See Literature Reference No. 22).

Epidiolex, a drug made exclusively of CBD, has been approved for the treatment of epilepsy in humans; however, this drug does not contain THC and no one skilled in the art would be motivated to include THC if such a compound was used for dogs or other animals other than human. Indeed, THC is considered to be toxic for dogs and cats by the medical establishment. California has the most progressive rules for veterinary professionals related to *cannabis*, being the first and only state to allow veterinarians to even discuss (much less recommend or prescribe) *cannabis* with their patients/clients (see Literature Reference No. 23). However, under this law, veterinarians are prohibited from dispensing or administering any *cannabis* or *cannabis* products.

In the past forty years of research, there have been multiple drugs approved for the treatment of epilepsy in veterinary medicine, however none of them are cannabinoids, terpenes or combinations thereof. Further, there have been no animal studies or any published reports on the use of Cannabinoid-Terpenoid compound therapy in the treatment of epilepsy in veterinary science. Therefore, there was little expectation that a CTS would reduce the frequency of seizures in dogs and cats. And no expectation whatsoever that a CTS would eliminate seizures in dogs and cats.

Antiepileptic drugs are commonly given orally for chronic treatment of epilepsy. The treatment of epilepsy requires administration of medications for both acute and chronic treatment using multiple types of formulations. Parenteral routes are used when the oral route is unavailable or a rapid clinical response is required. Lorazepam and Midazolam can be administered by the buccal, sublingual or intranasal routes. Consensus documents recommend rectal diazepam, buccal midazolam or intranasal Midazolam for the out-of-hospital treatment of early status epilepticus in humans. In the United States, diazepam is the only FDA approved rectal formulation. With the lack of parenteral, buccal or intranasal formulations for many of the antiepileptic drugs, the use of the rectal route of delivery to treat acute seizures or to maintain therapeutic concentrations is suitable for many, but not all antiepileptic medications. There is a significant need for new non-oral formulations of the antiepileptic drugs when oral administration is not possible. Addressing this need, the present invention also provides for oral-mucosal delivery, which was proven to be effective.

To show the effectiveness of the formula and solution of the present invention, a study was performed in which companion animals – canines and felines with existing epilepsy issues were examined. Prior to the study, several companion animals were taking concomitant AEDs. These included: Phenobarbital, Levetiracetam, Phenobarbital, Prednisone, Levetiracetam, Diazepam, Prednisone, Zonisamide. Some were taking multiple AEDs at once. Of those taking AEDs, the majority took either Phenobarbital and Prednisone to both. The animals were then treated with the CTS as described herein and, unexpectedly, were provided with a dramatic improvement in their seizures. FIG. 9 is a table depicting the experimental results of using a CTS according to the principles of the present invention in treating epilepsy in dogs.

As shown in FIG. 9, after three months of therapy, 11% of dogs had an equal or greater than 90% reduction in seizures. Remarkably, 97% of dogs were entirely free from seizures at the three-month stage. FIG. 9 also shows that after three months of therapy, 8% of cats had an equal or greater than 70% reduction in the number of seizures. Remarkably, 29% of cats had an equal or greater than 90% reduction in seizures and 63% of cats were entirely free from seizures at the three-month stage. Surprisingly, the treatment was very well-tolerated and associated with remarkable improvement, further demonstrating the efficacy of the CTS according to the principles of the present invention.

(B) Treatment of Anxiety

Veterinarians estimate that over half of dogs and cats suffer from fear, anxiety and stress, while noise aversion, specifically, is prevalent among dogs. Research shows that nearly 70% of dogs in the United States suffer from one or more signs of noise aversion. These issues, often misunderstood to be behavioral problems are, in reality, medical issues. Regular exposure to anxiety-inducing stimuli over a period of time can negatively affect the physical, mental or social health of the dog and thus reduce the quality of life.

Over the past forty years, there have been a number of studies on the use of the non-psychoactive Cannabidiol (CBD) to treat anxiety in humans. For example, CBD was shown to be helpful for decreasing anxiety through a simulated public speaking test at doses of 300 mg to 600 mg in single-dose studies. Other studies suggest lower doses of 10 mg/kg having a more anxiolytic effect than higher doses of 100 mg/kg in rats.

There are anecdotal reports of over-the-counter hemp CBD being used to treat anxiety. However, there have been no studies or any published reports on the use of CBD or Cannabinoid-Terpenoid compound therapy in the treatment of anxiety in veterinary science.

Based on human studies, dosage ranges for dogs have been suggested to be approximately 0.1 – 0.25 mg/kg of pet's body weight per day of THC and approximately 0.1 – 0.5 mg/kg of pet's body weight per day of CBD. However, THC is considered toxic for use in veterinary medicine, as discussed.

In the past forty years of research, there have been multiple drugs approved for the treatment of anxiety in veterinary medicine such as Xanax. Most recently, in 2016, the FDA approved the drug Sileo for noise aversion; however, none of the approved drugs are cannabinoids, terpenoids or combinations thereof.

Therefore, there was little expectation that a CTS would reduce anxiety in dogs or in cats. Further, there was no expectation whatsoever that the CTS would eliminate the symptoms of anxiety far better than an isolate solution of CBD hemp oil isolate solution with less than 0.3% THC. Moreover, there was no expectation that the effective dose of the cannabinoid-terpenoid solution with CBD, THC and terpenoids would contain over 50% fewer total cannabinoids than CBD isolate solution with less than 0.3% THC.

The results of an experimental study using CBD dominant compound were quite unexpected, yet extraordinarily positive. 219 dogs participated in a study on the effectiveness of the cannabinoid-terpenoid solution in the treatment of anxiety. 40 of the participating dogs were treated with a CBD isolate solution derived from hemp with less than 0.3% THC at a dose of 2 mg/kg q12H or every 12 hours. The remaining 179 dogs were treated with a CBD dominant cannabinoid-terpenoid formulation at a therapeutically effective dose q12H.

Functional alertness was measured on a scale from 1-4 order to check for intoxication or any sedative effects. The pet owners were responsible for administering the formulations to their pets, reporting the baseline prior to treatment and reporting the treatment results, which are depicted in the tables shown in FIGS. 12 through 14. Surprisingly, and as shown in FIG. 12, the canines treated with the CTS not only had far fewer symptoms of anxiety than those who were treated with the CBD isolate solution, but none of the dogs suffered any intoxicating or sedative effects from the THC in the CTS.

Also, as shown in FIG. 12, over 77% of the canines treated with the CTS reported (by the pet owner) an excellent response and 98% reported a good to excellent response to treatment for their anxiety. In sharp contrast, fewer than 25% of the canines treated with the CBD hemp oil reported good to excellent results with almost 23% reporting none to negative results.

Moreover, even though the canines treated with the CTS received a dose with less than 4 times the CBD (and fewer cannabinoids overall), compared to the CBD isolate solution, surprisingly, they exhibited fewer symptoms of anxiety and a better outcome. Therefore, not only was the CTS more effective without causing intoxication or sedation, but the CTS delivered therapeutic relief with a significantly reduced the overall cannabinoid amount for an effective dose.

(B) Treatment of Pain and Inflammation (e.g., Osteoarthritis)

As referenced above, the present disclosure provides a method for treating pain and/or inflammation in a non-human mammal in need thereof. The method comprises administering to a non-human mammal a pharmaceutical composition comprising a therapeutically effective amount of a lipophilic cannabinoid-terpenoid solution. Also provided herein are pharmaceutical compositions for treating pain or inflammation in a non-human animal in need thereof. The pharmaceutical compositions comprise a therapeutically effective amount of the CTS and an excipient, including any desired flavorants.

The CTS according to the principles of the present invention was shown to provide an unexpected, yet dramatic improvement over the prior art in treating pain and inflammation. Notably, with pain and inflammation (for example in the treatment of osteoarthritis), a THC balanced to THC dominant formulation was unexpectedly shown to be the most effective. Thus, this formulation achieves therapeutic efficacy with a fraction of the cannabinoid content (same terpene content) as the other two formulations (CBD Dominant, CBD Rich) and balanced CBD:THC ratio of 1:1. Moreover, the formulation, combined with method of increased delivery, achieves efficacy at 50 times fewer overall cannabinoids per dose than CBD alone; and, counter to any studies with CBD:THC to reduce pain in humans, the cannabinoid-terpenoid solution is effective with fewer, not more cannabinoids Due to the 50-fold difference referenced above, the formulation and dosage are beyond any possible prior art range. There is no reasonable expectation that anything within the claimed dosage range would work at such low concentrations. Also, because of THC toxicity and *cannabis* biphasic nature, there is no reasonable expectation that an effective ratio and dose would be easily discoverable (meaning that one skilled in the art would not naturally add THC; and even if one did add THC, one skilled in the art would anticipate using more cannabinoids together with CBD rather than fewer). Further, terpenoids are added for the extensive reasons stated herein; however, such an addition would not be obvious to one skilled in the art because they are not good for cats, generally and have most recently been shown not to mediate an entourage effect by acting at cannabinoid receptors.

Inflammation is the causal root of many diseases and health conditions. The immune system is, in part, regulated by the immunomodulatory effect of the endocannabinoid system as determined from in vivo and in vitro studies. Experimental models for a variety of autoimmune diseases have determined that cannabinoids are key players in multiple sclerosis, rheumatoid arthritis, colitis hepatitis, and psoriasis.

Cells of the immune system have been found to have the cannabinoid receptor CB2 present on their cell membrane. These CB2 receptors function to modulate a healthy response to inflammation by up-regulating several anti-inflammatory pathways, including the inhibition of T-cell pro-inflammatory activity. T-cell anti-inflammatory mechanisms affected by CB receptor agonists:
 1. Apoptosis of T-cells
 2. Suppression of pro-inflammatory cytokines and chemokines
 3. Inhibition of T-effector cell proliferation
 4. Promote the proliferation of T-regulatory cells.

The *cannabis* plant contains many molecules that reduce inflammation. The three major groups of molecules found in the *cannabis* plant are Phytocannabinoids, terpenes, and flavonoids, which all have strong anti-inflammatory properties. Phytocannabinoids activate CD95, which then induces both Bcl-2 and caspase cascades that lead to the apoptosis of immune cells. Phytocannabinoids can increase the production of IL-10, which has anti-inflammatory properties at the same time as they can reduce the manufacture of TNF-α and other pro-inflammatory cytokines.

Pharmaceutical NSAIDs use the endocannabinoid system in the creation of their anti-inflammatory effect. Acetaminophen is metabolized in the liver, and its by-product, N-arachidonoylphenolamine, functions both as a cannabinoid receptor agonist and as an eCB re-uptake inhibitor. Arachidonic acid can be converted to pro-inflammatory eicosanoids. However, arachidonic acid is also the major precursor in the production of the anti-inflammatory endocannabinoids, anandamide, and 2-AG. Normally, COX enzymes speed up the degradation of anandamide, which contributes to pain and inflammation. Non-steroidal anti-inflammatory drugs are COX-2 inhibitors that work, in part, by reducing the enzymatic degradation of the endocannabinoid anandamide.

In addition to the anti-inflammatory activity of phytocannabinoids, the terpenes and terpenoids found in the *cannabis* plant also have potent anti-inflammatory activity. Their anti-inflammatory effect is caused by the binding of certain terpenes to prostaglandin receptors, PGE1 and/or PGE2.

Terpenes most responsible for anti-inflammatory activity are:
 1. α-pinene
 2. β-myrcene
 3. β-caryophyllene
 4. limonene Osteoarthritis (OA) is a progressive and irreversible inflammatory condition of the joints which involve progressive loss of articular cartilage and new bone formation which leads to pain and stiffness in the joints. Any joint can be affected including hips, knees, elbows and the spine. Inflammation can be due to changes related to aging of the cartilage, an acute injury, or joint malformation. It is estimated that 20% of middle-aged dogs and 90% of senior dogs are affected by osteoarthritis. Certain breeds, like German shepherds, Labrador retrievers and Golden Retrievers are more likely to be affected. Despite common misconceptions, cats are similarly affected by osteoarthritis, but are less likely to show overt clinical signs like lameness although one study found 90% of cats over the age of 10 showed evidence of OA on X-rays. The primary cause of OA often cannot be identified in cats and the disease is less well understood compared to dogs.

Pain control is a mainstay of osteoarthritis treatment. The most commonly used pain control medications for more severe osteoarthritis are Non-Steroidal Anti-Inflammatory Drugs (NSAIDs). NSAIDs can not only reduce pain, but also decrease inflammation in the joints. However, NSAIDs have significant side effects with continued use, particularly in patients with poor liver or kidney function. Regular blood work may be needed in order to monitor the animal's health during NSAID therapy.

Other pharmaceuticals that can be considered are opioids such as codeine or Tramadol. However, opioids are not designed for chronic use. In addition, there has always been controversy over Tramadol's effectiveness and there is now consensus that it doesn't work well to control join pain. One recent study used both positive and negative controls (placebo) and found that there was no improvement in peak vertical force or vertical impulse in dogs on tramadol versus placebo.

NSAIDS like Meloxicam and Robenacoxib are effective for the treatment of acute pain, potential toxicity deters many veterinarians from long-term use, especially if a cat has kidney disease. Research regarding safety and dosing of these medications for OA in cats is ongoing.

U.C. San Diego researchers conducted a randomized controlled trial in human volunteers and like many studies, confirmed *cannabis* is effective for pain relief — but within a narrow therapeutic window (the range in which a drug is effective). Participants found no relief in either the placebo or low dose THC. The medium dose produced the most significant relief, while participants consuming the high THC dose *cannabis* experienced more pain.

GW Pharma came to similar conclusions when conducting clinical trials for Sativex, a 1:1 THC/CBD oromucosal spray. Participants were given three daily dose ranges: low-dose (1-4 sprays), mid-dose (6-10 sprays), and high-dose (11-16 sprays). Predictably, low and mid dose groups achieved superior results over the placebo, while high-dose patients experienced more adverse effects (22% dropped out).

While THC and CBD have different pharmacological properties, they can both have similar physiological effects, probably acting through different mechanisms. For instance, both compounds can have analgesic and anti-inflammatory effects; they may act through different mechanisms, so having THC and CBD could potentially enhance an outcome surrounding pain relief. As discussed above, THC is widely thought to be toxic for animals. However, the presence of CBD may have a significant impact on the psychoactivity of THC.

Yet, no studies have been conducted on the use of CBD, THC or terpenoids in the reduction of pain and inflammation in companion animals. And while a 2018 study, titled "Pharmacokinetics, Safety, and Clinical Efficacy of Cannabidiol Treatment in Osteoarthritic Dogs," led by Dr. Joseph Wakshlag of Cornell University showed promising results in the use of CBD hemp isolatetogether with NSAIDs in a small sample of dogs, the dose of CBD was more than 50-fold that of the CTS with a therapeutically effective dose of 0.4-0.8 mg/kg versus the 4 mg/kg used in the Cornell study. Furthermore, in human patients, there is an increase of overall cannabinoids when combining THC and CBD for the treatment of pain. For example, in a study of 177 patients with cancer pain, one group received an oral spray of THC, while another group perceived an oral spray of combined THC and CBD at an approximate 1:1 ratio. Both groups were allowed to gradually increase their dose until they experienced satisfactory relief. The THC group ended up using an average of 27 mg daily, while the CBD and THC group used close to 60 total mg daily, but the CBD and THC group had superior reduction in pain.

Figure 16:
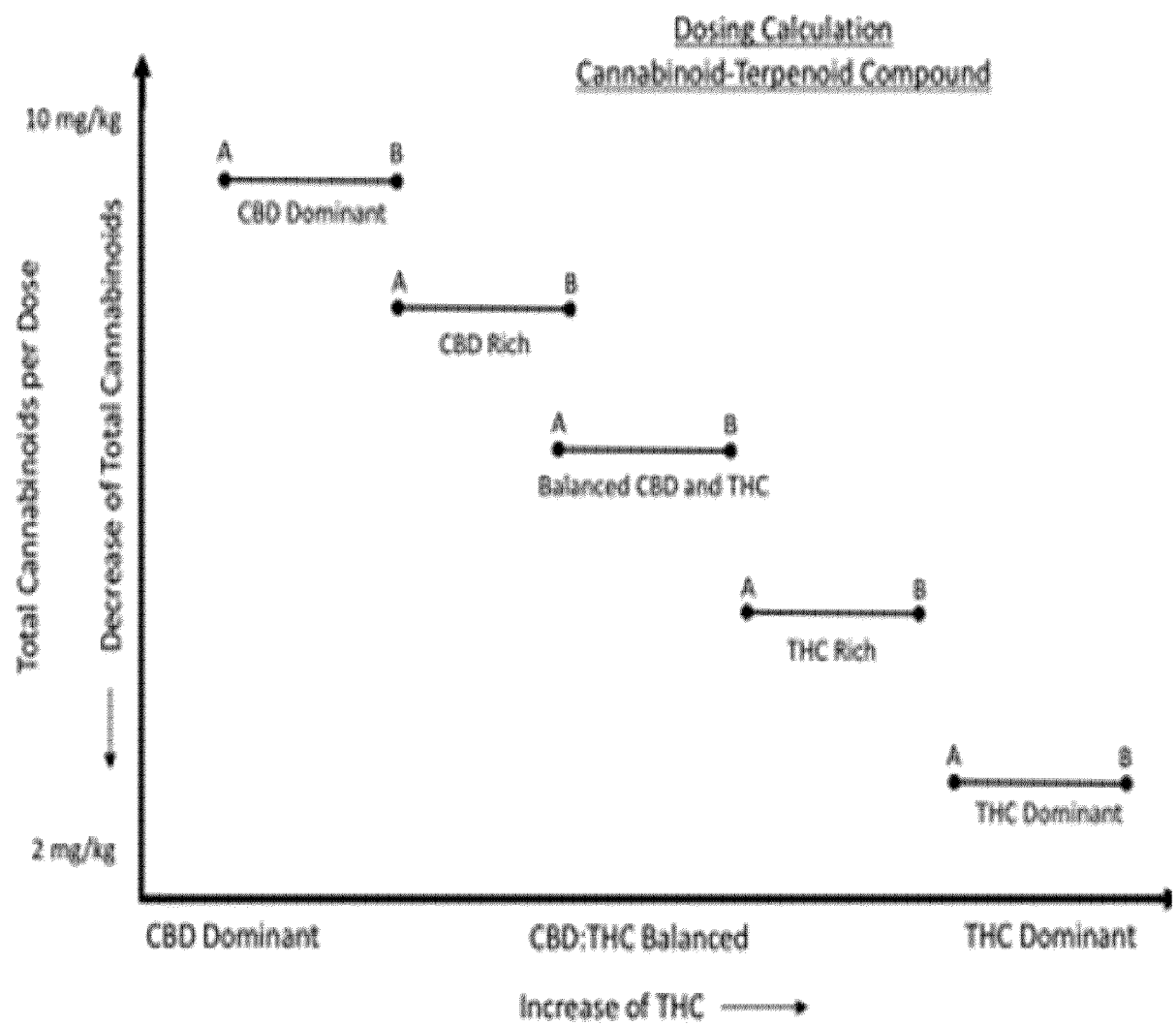
FIG. 16 is a graph depicting a decrease in overall cannabinoids per dose according to the CTS of the present disclosure, showing that as the ratios become more THC dominant, the overall cannabinoids decrease.

Therefore, there was little expectation that a CTS would be highly effective in reducing pain and inflammation in dogs and cats. There was also no expectation whatsoever that an effective dose would be 50-fold fewer total cannabinoids than previously thought and that higher THC levels would result in fewer overall cannabinoids per dose in companion animals versus humans where the overall cannabinoids per dose is increased not decreased. This finding is especially surprising given the use of canine models with naturally occurring OA disease for human medicine due to the many similarities between the canine and human species with respect to OA. For example, FIG. 15 is a graph depicting the overall cannabinoids increase for humans and animals in prior art as CBD and THC are taken consecutively/simultaneously. Further, FIG. 16 is a graph depicting the unexpected discovery that when taking the CTS of the present disclosure, as THC increases, the overall total cannabinoids per effective treatment dose decrease instead of increase.

Moreover, those companion animals who began the study taking other drugs such as NSAIDS or opiates, surprisingly found no need to continue those drug protocols in favor of the cannabinoid-terpenoid solution. To show the effectiveness of the formula and solution of the present invention, a study was performed in which companion animals with diagnosed osteoarthritis were examined. Prior to the study, several companion animals were taking concomitant NSAID drugs. These included: Meloxicam, Gabapentin, Carprofen and Robenacoxib. Some were taking Tramadol and other opiates. There was a wide heterogeneity of osteoarthritis signs and symptoms among and between the dogs and cats. FIG. 17 is a table depicting the characteristics of the study participants.

Cats, unlike most dogs, can tolerate severe orthopedic disease due to their small size and natural agility. Changes to osteoarthritis-affected joints in cats are usually subtle. Decreased range of joint motion, commonly seen in dogs, is uncommon in cats. Clinical signs of osteoarthritis in cats include weight loss, loss of appetite, depression, change in general attitude, poor grooming habits, urination or defecation outside the litter pan, and inability to jump on and off objects.

Several studies have been conducted evaluating radiographic changes associated with osteoarthritis in cats. In general, radiographic changes observed in cats with osteoarthritis are less severe than those observed in dogs with osteoarthritis. In many cases, cats with osteoarthritis have no radiographic changes. For example, in one study, 229 out of 292 cats with osteoarthritis had no radiographic evidence of the disease, while evidence was present in the other 63 cats. Thus, an owner assessment was collected indicating the sign prevalence and perception of response to therapy. See, for example, FIG. 18, which is a chart depicting the experimental results of using a compound(s) according to the principles of the present invention in treating pain and inflammation in cats.

The dogs and cats were treated with the CTS as described herein and, unexpectedly, were provided with a dramatic improvement in their conditions. Owner reported canine brief pain inventory (CBPI) scores showed a surprisingly large increase in comfort, activity and overall quality of life in the home environment over a 12-week period.

Figure 18:
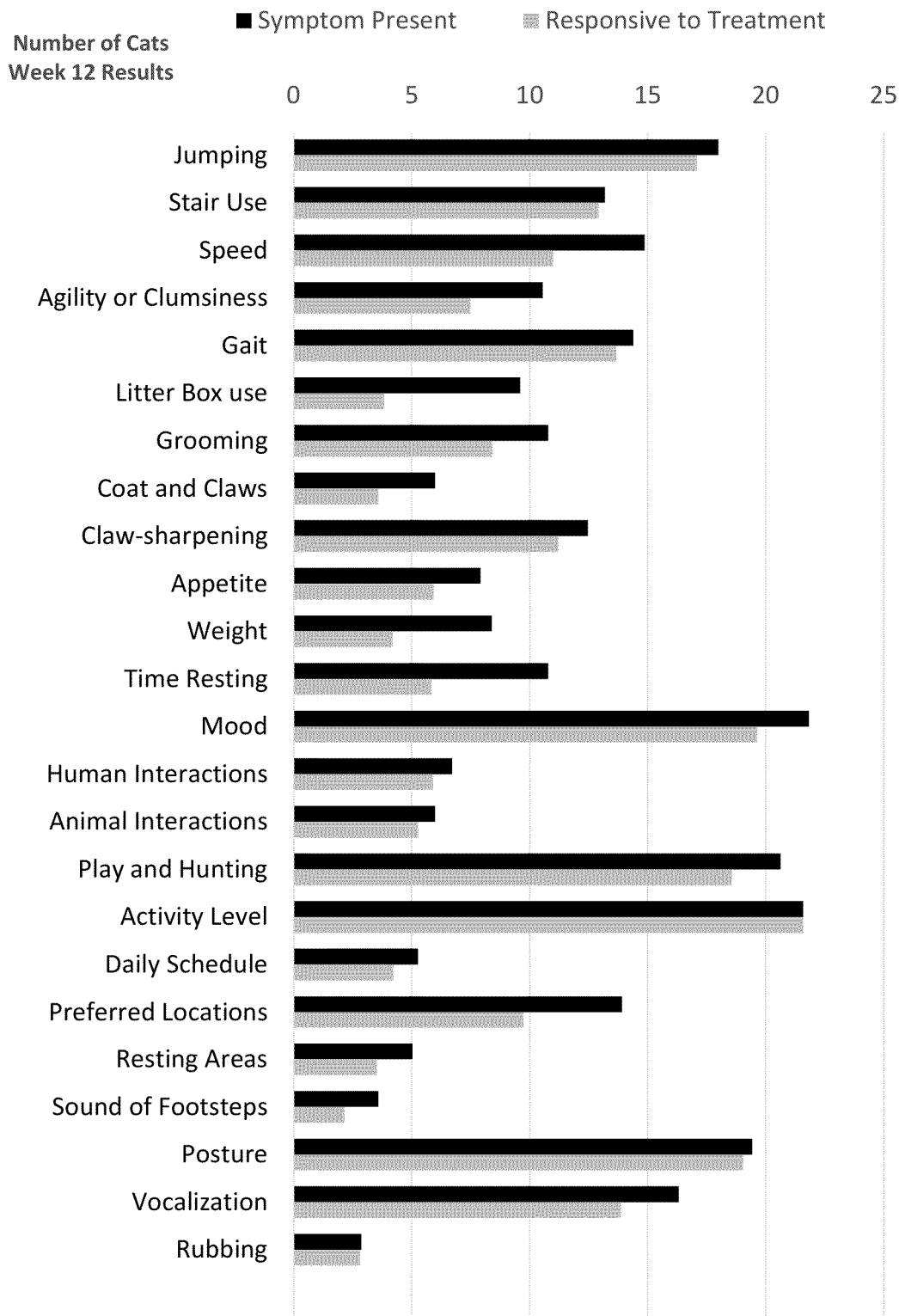
FIG. 18 is a chart depicting the experimental results of using a CTS according to the principles of the present invention in treating pain and inflammation in cats.

FIG. 19, for example, is a table depicting the experimental results of using the CTS according to the principles of the present invention in treating pain and inflammation in dogs, while FIG. 18 depicts the results in cats.

As shown in FIG. 19, surprisingly, in the first month of treatment with the CTS, the mean CBPI Pain index went down significantly by 54% from 24 to 11 for all dogs. By the end of the three-month period, the overall CBPI Pain index went down by 83% from 24 to 4. Furthermore, the activity inference in the first month of treatment with the CTS, the mean CBPI Activity Inference index went down significantly by 55% from 38 to 17 for all dogs. By the end of the three-month period, the overall CBPI Activity Inference index went down by 84% from 38 to 6. Remarkably, the overall quality of life score doubled in the first month of treatment with the cannabinoid-terpenoid solution and by the end of the three-month period, the mean overall quality of life score increased to 5 or excellent.

FIG. 18 shows that after three months of therapy, a remarkable 100% of cats had a significant response to treatment with over 90% improvement to almost half of the symptoms measured.

Surprisingly, not only was the treatment very well-tolerated and associated with remarkable improvement in both canine and feline species, further demonstrating the efficacy of the cannabinoid-terpenoid solution or compound according to the principles of the present invention, but each group also had a significant number of reports of increased appetite during the treatment period whereas no such reports were received at non THC-dominant ratios. Thus, it is clear that the CBD:THC balanced, THC rich, and THC dominant compounds as described herein provided a marked and unexpected result in treating animals for pain and inflammation. It should be noted that the benefit noted begins with the CBD:THC balanced formulation and then continues through the THC dominant.

(C) Method for Applying the Compound to Increase Delivery

As noted above, the present invention also provides a unique method for delivering and applying the CTS to increase delivery. For example, the present invention relates to a chemical combination, and more particularly, to a chemical combination that when delivered transmucosally, increases stable solubility, absorption, and efficacy of the cannabinoid-terpenoid solution.

As can be understood by those skilled in the art, the solution or composition varies based on the condition being treated and a particular delivery method. The list below, although not limited thereto, illustrates desired compositions for some example delivery methods.

There currently exists a lack of bioavailability of cannabinoids, especially in the oral forms available as CBD treats. Tests have shown that at best 15-20%, but on average only 5-10% of the CBD administered orally is ultimately being absorbed.

Oromucosal administration is a novel way to deliver CTS in non-human mammals. The oral mucosa is an appropriate route for drug delivery systems, as it evades first-pass metabolism, enhances drug bioavailability and provides the means for rapid drug transport to the systematic circulation. This delivery system offers a more comfortable and convenient delivery route compared with the intravenous route.

Bioavailability of the Cannabinoid-Terpenoid solution varies greatly depending on the method of administration. The averages for Cannabinoid bioavailability by method of administration are: 5% – 10% for oral (swallowed and digested by the GI system) and 35%-90% for oromucosal (absorbed directly through the mouth).

In addition, the oral administration of drugs to animals is often troublesome as the animal being treated often refuses to receive the drug. Particularly in the case of domestic cats, drug therapy by means of oral administration of active ingredient is extremely complicated and difficult because it strongly opposes the intake of tablets. Even if the dosage form to be administered is mixed with the animal feed, this usually does not lead to success, since the animals selectively avoid the intake of the drug particles during feeding and only take up the drug-free feed. If, nevertheless, an oral ingestion should occur, the drug is often spit out immediately. Therefore, the pet owner must bring the dosage form directly deep into the throat of the animal and prevent the animal from spitting, if necessary by holding the snout. Furthermore, due to the circumstances mentioned, it is difficult to ensure that the animal actually receives the intended dose of active substance.

The present invention addresses these issues by providing a unique chemical combination that, when delivered transmucosally, increases stable solubility, absorption, and efficacy of the CTS. An object of the present invention is, therefore, to provide a dosage form and method of administration, which avoids or at least reduces the above-mentioned problems in the administration of the CTS to cats and dogs, in particular during oral administration. The present invention allows for application directly to oral mucosa. In particular, in some aspects, the present invention provides for a solution which is administered to the oral cavity mucosa specifically by application to the buccal or ginvial mucosa, whereby transmucosal absorption of a pharmaceutically effective amount. By administering the CTS of this invention, a method is provided to achieve higher CTS plasma concentration at lower single doses. In other words, this invention allows increased bioavailability of the CTS in animals.

It is an object of the present invention to provide oromucosal compositions which achieve therapeutic plasma levels of the CTS in animals without depending on feed intake. Such compositions are described throughout this disclosure, including at least any of the CBD dominant, CBD rich, CBD:THC balanced, THC rich, and THC dominant formulas. The compositions of the present invention may be administered to the lingual, sublingual, sublabial, palatal and pharyngeal mucosa, but are preferably administered to the buccal or gingival mucosa. A single dose of the compositions of the present invention may be distributed to multiple mucous membranes. For example, the compositions can be administered to both the buccal and gingival mucosa.

The CTS of the present invention also includes one or more pharmaceutical carriers or excipients, adjuvants or penetration enhancers which are collectively referred to as carriers (or excipients). The intended function of an excipient is to act as the carrier (vehicle or basis) or as a component of the carrier of the active substance(s). These carriers or excipients are, in some aspects, desirably formulated for transmucosal administration, preferably for the safe and therapeutically effective administration to the oral mucosa and especially to the buccal mucosa. Thus, in some embodiments, the excipient is a lipophilic carrier such as MCT oil or any other binder (carrier) to bind the CBD and THC into a suitable form for administration to the oral mucosa and especially to the buccal mucosa.

In another aspect, the compositions of the present invention as described throughout this disclosure may also contain stabilizing agents in addition to CTS and the aforementioned excipients. Non-limiting examples of such stabilizers include gum arabic, polyvinyl alcohol (PVA), polysorbate 80 or glycerol.

In yet another aspect, the compositions of the present invention may also contain preservatives in addition to the CTS and the aforementioned excipients as described throughout this disclosure. Non-limiting examples of such preservatives include ethanol (in sufficient concentration) benzyl alcohol and sodium benzoate.

The compositions of the present invention may contain, in addition to CTS and the abovementioned excipients, water-soluble and / or ethanol-soluble mucoadhesive polymers. Non-limiting examples of such for mucoadhesive polymers include hydroxypropylmethylcellulose or gum arabic.

The compositions of the CTS of present invention are in a desired embodiment transmucosal solutions, and are formulated for oromucosal administration. The transmucosal absorption rate of CTS through the oral mucosa is increased by increasing the contact surface of the oral mucosa with the compositions. Therefore, the transmucosal compositions of this invention should desirably be administered directly to the surface of the oral mucosa.

Transmucosal administration of the CTS of the present invention has increased bioavailability, requires lower single doses, and achieves the maximum plasma concentration more rapidly than with the administration of the conventional peroral CBD. This allows CTS to be administered with lower single doses.

Thus, while oral mucosal delivery is desired and described above, it should also be understood that the CTS of the present invention can be formed in any suitable form that allows for enhanced delivery, several additional non-limiting examples include;
1. Oral Delivery: Mucoadhesive/super-disintegrating tablets; bi therapy tablets; mucoadhesive films / patches / wafers; sublingual capsules; gels; sprays; Buccal mucosal drug delivery systems (buccal film/patch & buccal tablet).
2. Intranasal Delivery: Nasal sprays; foams; aerosols; patches; nano-carrier-loaded films; in-situ gels; hydrogels.
3. Ocular Delivery: Drops; gels; solutions; patches; films.
4. Vaginal Delivery: Pessaries; vaginal rings; vaginal gels; vaginal sprays; vaginal foams.
5. Rectal Delivery: Suppositories; rectal capsules; rectal tablets; gels; films; multi-layered patches.
6. Pulmonary Delivery: Aerosols; sprays; DPI.

As noted above, the present disclosure also provides a method for applying the compound to effectively treat a variety of diseases and disorders through a variety of delivery techniques that have provided unexpected, yet extraordinary, results.

(D) Method of Dosing to Effectively Treat the Diseases and Disorders

Most medications have a monophasic dose-response relationship meaning, a higher dose will result in a stronger therapeutic effect (and a higher likelihood of adverse effects). *Cannabis* does not follow this pattern and is characterized by a biphasic dose-response relationship meaning, a higher dose will first result in stronger effects, but subsequent dosage increases can result in weaker and weaker therapeutic effects (accompanied by an increase in unwanted effects).

In a study of 263 opioid-treated cancer patients with poorly controlled pain, the group receiving 21 mg of combined THC and CBD each day experienced significant improvements in pain levels, more so than the group that received 52 mg daily. The group that received 83 mg daily reduced their pain no better than placebo, but experienced more adverse effects.

The term "therapeutic window" describes the range between the lowest effective dose and the dose that produces unwanted or intolerable side effects. While there is no therapeutic window for *cannabis* use in animals, a general guide based on human dosing appears to be between 0.1-0.25 mg/kg of a pet's body weight per day for THC and between 0.1-0.5 mg/kg of a pet's body weight per day for CBD.

*Cannabis* also has the ability to produce opposite or bidirectional effects in humans. For example, some anxious people who take *cannabis* to relax might benefit from a dose which makes non-anxious people taking the same dose, anxious. Interestingly, the symptoms of *cannabis* overdose in people closely mirror the symptoms one would expect *cannabis* to relieve at appropriate doses: nausea, vomiting, diarrhea, sweating, spasms, tremors, anxiety, panic attacks, paranoia, dis-coordination, and disturbed sleep.

In humans, studies have shown that CBD and THC have many overlapping therapeutic qualities, including relief of pain, anxiety, seizures, and nausea, although they work via different mechanisms of action. When combined, CBD and THC can enhance each other's benefits, or potentiate one another, while reducing unwanted effects. Thus, by adding CBD to THC, the therapeutic window, described above, becomes even wider. However, the total dose of cannabinoids needed to treat a symptom or condition also increases in humans.

For example, in a study of 177 patients with cancer pain, one group received an oral spray of THC, while another group received an oral spray of combined THC and CBD at an approximate 1:1 ratio. Both groups were allowed to gradually increase their dose until they experienced satisfactory relief. The THC group ended up using an average of 27 mg daily, while the CBD+THC group used close to 60 total mg daily, but the CBD+THC group had a superior reduction in pain.

Surprisingly and as depicted in FIG. 10, it was determined through experimental results that the opposite occurred with respect to therapeutically effective doses for companion animals. As the THC was increased in the CTS, the number of overall cannabinoids that are needed to provide an effective does is decreased significantly.

Today's drug development is commonly based on a "one-size-fits-all" concept. The traditional concept of "one-size-fits-all" provides an inadequate dosing paradigm requiring new approaches in order to better identify optimal drug doses. Personalized medicine is based on the belief that different people respond differently to a drug, resulting in positive responses to a drug by some individuals but not others. Today, adverse drug effects are the fifth leading cause of deaths in the United States and clinical trial data suggests that more than 2 million serious adverse events occur each year resulting in more than 100,000 deaths.

The varying drug responses among patients could be attributed to intrinsic ethnic factors such as genetics, metabolism or elimination. Drug responses could also be affected by extrinsic factors associated with environment or culture such as medical practice, diet, or alcohol use. However, there are currently no known biomarkers or methods that can predict which group of patients will respond positively, which patients will be non-responders, and which patients will experience adverse effects. Hence, new research is needed to study the effects of an individual's genetic makeup on responses to various drugs (i.e.,pharmacogenetics-investigates the relationship between drug responses and genetic differences; pharmacogenomics-a genome-wide approach that studies the entire spectrum of genes involved in drug responses).

Pharmacokinetic principles may also be used to design dosage regimens for individual patients in order to achieve therapeutic plasma concentrations of drugs. drugs. Such designs would require the estimated kinetic data of the drug in the patient and a therapeutic range.

The seminal example is Warfarin, a drug for treating thromboembolism, which has a fixed dose of 5 mg/day and an average maintenance dose of 4-6 mg per day. The dose for different patients can range widely requiring anywhere between 4.5-77 mg per week, placing patients at risk because the correct dose cannot be determined for the vast majority of patients requiring treatment. Despite Warfarin's 60 years of existence, the problem of dosing lingers. There is a vast difference between discovering a molecule such as Warfarin and knowing how it affects patients and what doses are required for the desired effects. Warfarin is only therapeutically useful if it reaches an appropriate level of anticoagulation, losing its effectiveness at low levels. However, if anticoagulation levels are too high, there could be a significant risk of complications due to increased bleeding or hemorrhaging in patients.

*Cannabis*, as discussed, is individualized medicine and effective treatment is dependent not only on finding the dosage, but on finding the right cannabinoid-terpenoid formulation for a particular condition. In order to ascertain a pharmaceutically effective dose, in the very least, a base dosage range must be determined. Thus, the present invention provides several unique and unexpected dosages, as depicted in FIG. 10.

(E) Database Generation and Collection System

As noted above, the present invention also includes a master database generation and collection system that receives experimental and/or clinical data to ensure accurate compound dosing, treatments, pharmacovigilence and study design. Thus, the invention includes a method for compiling and generating data, including Real World Data both before and after the medication is administered among medical doctors, including veterinarians, laboratories, patients and in the case of humans and mammals other than humans, pet owners, where a software working with a wearable technology activity tracker allowing integration of tracker data with the reporting of information used to monitor dosage and result, along with blood work, various data points such as breed, diagnosis, age, other medications, food and water intake, environmental conditions in order to optimize dosage among different people and different animal species, breeds and conditions or ailments. The software is configured to provide an alert where the wearer is taking medication which has a negative interaction with a new medication, supplement or food. The software also tracks improvement of symptoms and compares the information among a larger population to develop a minimum effective dose of a newly introduced medicine where, for example, that medicine has a dosage range and that medicine is *cannabis* derived. The software is also configured to generate personalized medicine as well as clinical trial design.

List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Russo EB. Taming THC: potential *cannabis* synergy and phytocannabinoid-terpene entourage effects. Br J Pharmacol. 2011;163(7):1344-1364.
2. DB F, KJ S, M N, C J, M G. Terpenes from *Cannabis* Do Not Mediate an Entourage Effect by Acting at Cannabinoid Receptors. Frontiers in pharmacology. 2020;11.
3. Gaoni Y., Mechoulam R. Isolation, structure, and partial synthesis of an active constituent of hashish. J. Am. Chem. Soc. 1964;86:1646-1647. doi: 10.1021/ja01063046.
4. Matsuda L.A., Lolait S.J., Brownstein M.J., Young A.C., Bonner T.I. Structure of a cannabinoid receptor and functional expression of the cloned cDNA. Nature. 1990;346:561–564.
5. Munro S., Thomas K.L., Abu-Shaar M. Molecular characterization of a peripheral receptor for cannabinoids. Nature. 1993;365:61–65.
6. Mackie K. Cannabinoid receptors as therapeutic targets. Ann. Rev. Pharmacol. Toxicol. 2006;46:101–122.
7. Azad S.C., Monory K., Marsicano G., Cravatt B.F., Lutz B., Zieglgansberger Rammes G. Circuitry for Associative Plasticity in the Amygdala Involves Endocannabinoid Signaling. J. Neurosci. 2004;24.
8. Khasabova I.A., Khasabov S.G., Harding-Rose C., Coicou L.G., Seybold B.A., Lindberg A.E., Steevens C.D., Simone D.A., Seybold V.S. A Decrease in Anandamide Signaling Contributes to the Maintenance of Cutaneous Mechanical Hyperalgesia in a Model of Bone Cancer Pain. J. Neurosci. 2008;28:11141-11152.
9. Gray J.M., Vecchiarelli H.A., Morena M., Lee T.T.Y., Hermanson D.J., Kim A.B., McLaughlin R.J., Hassan K.I., Kuhne C., Wotjak C.T., et al. Corticotropin-Releasing Hormone Drives Anandamide Hydrolysis in the Amygdala to Promote Anxiety. J. Neurosci. 2015;35:3879–3892.
10. Nakajima Y., Furuichi Y., Biswas K.K., Hashiguchi T., Kawahara K., Yamaji K., Uchimura T., Izumi Y., Maruyama I. Endocannabinoid, anandamide in gingival tissue regulates the periodontal inflammation through NF-κB pathway inhibition. FEBS Lett. 2006;580:613–619.
11. Malek N., Popiolek-Barczyk K., Mika J.P., Starowicz K. Anandamide, Acting via CB2 Receptors, alleviates LPS-Induced Neuroinflammation in Rat Primary Microglial Cultures. Neural Plast. 2015:130639.
12. Sulcova E., Mechoulam R., Fride E. Biphasic Effects of Anandamide. Pharmacol. Biochem. Behav. 1998;59:347–352.
13. Jesudason D., Wittert G. Endocannabinoid system in food intake and metabolic regulation. Curr. Opin. Lipidol. 2008;19:344–348.
14. Smith M., Wilson R., O'Brien S., Tufarelli C., Anderson S.I., O'Sullivan S.E. The Effects of the Endocannabinoids Anandamide and 2-Arachidonoylgylcerol on Human Osteoblast Proliferation and Differentiation. PLoS ONE. 2015;10:e0136546.
15. Hartsel J.A., Boyar K., Pham A., Silver R.J., Makriyannis A. *Cannabis* in Veterinary Medicine: Cannabinoid Therapies for Animals. In: Gupta R.C., Srivastava A., Lall R., editors. Nutraceuticals in Veterinary Medicine. Springer; Berlin/Heidelberg, Germany: 2019. pp. 121–155.
16. Herkenham M., Lynn A.B., Little M.D., Johnson M.R., Melvin L.S., de Costa B.R., Rice K.C. Cannabinoid receptor localization in brain. Proc. Natl. Acad. Sci. USA. 1930;87:1932-1936. doi: 10.1073/pnas.87.5.1932.
17. 83. Hill M.N., McLaughlin R.J., Morrish A.C., Viau V., Floresco S.B., Hillard C.J., Gorzalka B.B. Suppression of amygdalar endocannabinoid signaling by stress contributes to activation of the hypothalamic-pituitary-adrenal axis. Neuropsychopharmacology. 2009;34:2733. doi: 10.1038/npp.2009.114.
18. Pertwee R.G. Cannabinoid receptors and pain. Prog. Neurobiol. 2001;63:569–611. doi: 10.1016/S0301-0082(00)00031-9.
19. Silver, R.J. Medical Marijuana and Your Pet Morrisville, NC:Lulu Publishing Services 2015:47
20. Thompson, Comparison of Acute Oral Toxicity, July 1973.
21. Hill M.N., McLaughlin R.J., Morrish A.C., Viau V., Floresco S.B., Hillard C.J., Gorzalka B.B. Suppression of amygdalar endocannabinoid signaling by stress contributes to activation of the hypothalamic-pituitary-adrenal axis. Neuropsychopharmacology. 2009;34:2733.
22. McGrath S., Bartner L.R., Rao S., Kogan K.R., Hellyer P.W. A Report of Adverse Effects Associated with the Administration of Cannabidiol in Healthy Dogs. J. AHVMA. 2018;52:34-38.
23. On Sep. 27, 2018, Governor Edmund G. Brown Jr. signed into law Assembly Bill 2215 (Kalra, Chapter 819, Statutes of 2018). AB 2215 became effective Jan. 1, 2019. This bill amends section 4883 of, and adds section 4884 to, the BPC relating to veterinarians.

Glossary

A glossary is provided in which various terms used herein and in the claims are defined. The glossary provided is intended to provide the reader with a general understanding of the intended meaning of the terms, but is not intended to convey the entire scope of each term. Rather, the glossary is intended to supplement the rest of the specification in more accurately explaining the terms used.
1. (s) - The term "(s)" following a noun contemplates the singular or plural form, or both.
2. A, An, and The - It must be noted that as used herein and in the appended claims, the singular forms "a," "an," and "the" include plural reference unless the context clearly dictates otherwise. Thus, for example, a reference to "a fatty acid" and/or "at least one fatty acid" may include one or more fatty acids, and so forth.
3. Administering - The term "administering" refers to providing the composition to a subject suffering from or at risk of the disorders(s) and/or condition(s) to be treated.
4. And/or - The term "and/or" can mean "and" or "or".
5. Bioavailability - The term "bioavailability" in this disclosure refers to the physiological availability of a given amount of a drug as distinct from its chemical potency; proportion of the administered dose that is absorbed into the bloodstream.
6. Biphasic – "Biphasic" generally refers to the properties of *cannabis* compounds like THC wherein low and high doses of the same substance can produce the opposite effects.
7. Cannabinoid - The term "cannabinoid" in this disclosure refers to any of the diverse chemical compounds that act on cannabinoid receptors on cells in the brain, act on orthosteric or allosteric sites and modulate endocannabinoid activity. They include the phytocannabinoids found in *cannabis*, hempseed oil, other plants, and synthetic cannabinoids manufactured artificially. They include the phytocannabinoids delta-9-tetrahydrocannabinol (THC), cannabidiol (CBD), cannabinol (CBN) cannabigerol (CBG), cannabigerol (CBG), cannabichromene (CBC), cannabicyclol (CBL), canabivarol (CBV), tetrahydrocannabivarin (THCV), cannabidivarin (CBDV), cannabichromevarin (CBCV), cannabigerol monoethyl ether (CBGM), or the like; or mixtures or combinations thereof. Other botanical cannabimimetics include N-alkylamides from Echinacea and B-caryophyllene. They include mixtures of phytocannabinoids separated from the plant by extraction techniques and high purity cannabinoids obtained by purification from natural sources or via synthesis.
8. Cannabinoid Averse Effects - The term "cannabinoid adverse effects" in this disclosure refers to the adverse effect of cannabinoid therapy. These problems include impaired cognition, disruption of memory, behavioral changes, emotional changes, and cardiovascular effects, including increased heart rate, increased work-load, increased plasma volume and postural hypotension and developing a tolerance to cannabinoids.
9. Cannabinoid Therapy - The term "cannabinoid therapy" in this disclosure refers to the use of cannabinoids to prevent, treat and/or ameliorate and disease and/or pathology that includes and is not limited to Alzheimer Disease, Amyotrophic Lateral Sclerosis (ALS), chronic pain, diabetes mellitus, dystonia, epilepsy, fibromyalgia, gastrointestinal disorders, gliomas, cancer, Hepatitis C, Human Immunodeficiency Virus (HIV) Huntington Disease, hypertension, incontinence, methicillin-resistant Staphyloccus aureus (MRSA), multiple sclerosis, osteoporosis, pruritus, rheumatoid arthritis, sleep apnea and Tourette Syndrome.
10. *Cannabis* – The term "*cannabis*" is used herein to refer to all physiologically active substances derived from the *cannabis* family of plants and synthetic *cannabis* analogues and derivatives, precursors, metabolites etc., or related substances having *cannabis*-like physiological effects.
11. *Cannabis* Concentrate - The term "*cannabis* concentrate" in this disclosure refers to the cannabinoids of the *cannabis* plant that have been extracted using one of the many known extraction methods. In one embodiment *cannabis* concentrates refer to *cannabis* oil, budder, wax or shatter.
12. *Cannabis* Extracts - The term "*cannabis* extracts" in this disclosure refers to the cannabinoids of the *cannabis* plant that have been extracted and concentrated using one of the many known extraction methods including non-hydrocarbon solvent extracts from water, carbon dioxide and isopropyl alcohol; hydrocarbon solvent extracts from butane, propane, and hexane; and dry sieve method.
13. Cell Membranes - The terms "cell membranes", "biological barriers" and "mucosa barriers" in this disclosure refer to 1) the mucosal membrane barriers of the oral cavity; 2) the mucosal membrane barrier of the GI tract; 3) the dermal and epidermal cell membrane barriers; 4) the BBB; 5) the blood-ocular barrier consisting of the blood-aqueous barrier and the blood-retinal barrier; 6) ocular barriers of the conjunctiva and corneal epithelium; and 7) the mucosa of the nasal cavity 8) the cell membrane barriers of the nervous system, respiratory system, circulatory system, GI system, muscular system, urinary system, genital system, internal organs, and tissues.

14. Comprising - The term "comprising" is used in an inclusive sense, i.e. to specify the presence of the stated features but not to preclude the presence or addition of further features in various embodiments of the invention. When interpreting statements in this specification that include that term, the features, prefaced by that term in each statement, all need to be present but other features can also be present. Related terms such as "comprise" and "comprised" are to be interpreted in the same manner.

15. Delivers - For purposes of the present invention, the term "delivers" when used with respect to the topical formulation or transdermal therapeutic system means that the formulation or system provides a mean relative release rate or flux of the drug out of the formulation or system and through the skin of the patient.

16. Effective Amount - By "effective amount" it is meant an amount sufficient that, when administered to a subject, an amount of the composition is provided to achieve an effect. In the case of a therapeutic method, this effect may be the treatment of a pain, inflammation and/or anxiety, or to control a heart rate of a subject. Therefore, the "effective amount" may be a "therapeutically effective amount". By "therapeutically effective amount" it is meant an amount sufficient that when administered to a subject an amount of composition is provided to treat the disease, disorder and/or condition, or a symptom of the disease, disorder and/or condition.

17. Effective Amount - For purposes of the present invention, an "effective amount" of a permeation enhancer as used herein, for example, means an amount that will provide the desired increase in skin permeability and, correspondingly, the desired depth of penetration, rate of administration, and amount of drug to be delivered.

18. Highly Purified Cannabinoids - "Highly purified cannabinoids" are defined as cannabinoids that have been extracted from the *cannabis* plant and purified to the extent that other cannabinoids and non-cannabinoid components that are co-extracted with the cannabinoids have been removed, such that the highly purified cannabinoid is greater than or equal to 90% (w/w) pure.

19. Immediate Release - For purposes of the present invention, the term "immediate release" means that the cannabinoid drug(s) is administered at the site of application (e.g., the back of the neck) and is available for immediate absorption at the site of application. In other words, the term "immediate release" is meant to convey in terms of a topical formulation the fact that there is nothing in the formulation (e.g., a sustained release carrier) that would delay or slow the availability of the drug at the site of application (in contrast to, e.g., a transdermal device or patch).

20. Implantable - For purposes of the present invention, an "implantable" formulation includes, for example, a solid, semisolid or liquid drug formulation which can be administered at the back of the neck region either via injection and/or via surgical implantation. The solid may comprise microspheres, microcapsules, pellets, discs, and the like. The implantable formulations of the invention may provide a controlled or sustained release of the drug at the site of administration.

21. Injectable - For purposes of the present invention, an "injectable" formulation includes, for example, an injectable solution, suspension, gel or the like and may be in immediate release form or may provide a controlled or sustained release of the drug at the site of administration.

22. Ligand - The term "ligand" in this disclosure refers to any material that may be bound to the surface of the nanoparticle or nanostructure for the linking of nanoparticles to form nanometer-scale geometric structures.

23. Medium Chain Triglyceride - The term "medium chain triglyceride" (MCT) "in the present disclosure refers to a class of triglyceride oil that are derived from fatty acids that are usually about 8 to about 12 carbons in length and that can be added as an excipient to the formula comprising the CTS.

24. Minimally Effective Dose - For purposes of the present invention "minimally effective dose" or "therapeutically effective" or "effective" amount is meant to be a nontoxic but sufficient amount of a cannabinoid compound(s) to provide the desired therapeutic effect.

25. Mucous Release Formulation - For purposes of the present invention, a "mucous release formulation" includes, for example, an oral solution, suspension, gel, solid or the like and may be in immediate release form or may provide a controlled or sustained release of the drug at the site of administration.

26. Nutraceutically Acceptable - The term "nutraceutically acceptable" in the context of a form of a compound or an additive to the composition, is intended to mean that the form of the compound of the additive to the composition is suitable for use in a nutraceutical sense. Therefore, nutraceutically acceptable forms and/or additives are non-toxic to the subject in the amounts in which they are present in the composition described herein. It will be appreciated that all pharmaceutically acceptable forms and additives will typically also be nutraceutically acceptable.

27. Oral Formulation - For purposes of the present invention, an "oral" formulation includes, for example, an oral solution, suspension, tablet, capsule or the like and may be in immediate release form or may provide a controlled or sustained release of the drug. The additional inactive components that form the oral formulation in order to bind and provide immediate/controlled, or sustained release of the drug by oral delivery are well known to those skilled in the art and can be altered as need to provide for the oral solution, suspension, tablet, capsule or the like.

28. Oromucosal - For the purposes of the present invention, "oromucosal" is a delivery method relating to, being, or supplying a medication towards the mucous surfaces of the mouth.

29. Penetration or Permeation Enhancement - "Penetration enhancement" or "permeation enhancement" for purposes of the present invention relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal (mammal) skin using a diffusion cell apparatus.

30. Pharmaceutically Acceptable - The term "pharmaceutically acceptable" in the context of a form of a compound or an additive to the composition, is intended to mean that the form of the compound or the additive to the composition is suitable for use in a pharmaceutical sense. Therefore, pharmaceutically acceptable forms and/or additives are non-toxic to the subject in the amounts in which they are present in the compositions described herein. In some embodiments, the composition of the invention is a nutraceutical composition. It will be appreciated that any ingredient that is pharmaceutically acceptable will also be suitable for nutraceutical use.

31. Phytocannabinoids - "Phytocannabinoids" are cannabinoids that originate from nature and can be found in the *cannabis* plant. The phytocannabinoids can be isolated from plants to produce a highly purified extract or can be reproduced synthetically.

32. Synthetic Cannabinoids - "Synthetic cannabinoids" are compounds that have a cannabinoid or cannabinoid-like structure and are manufactured using chemical means rather than via plant extraction.

33. THC Toxicity - "THC Toxicity" includes symptoms of panting (in canines), anxiety, and extreme agitation; dilated pupils, glossy-eyes, and a "dazed and confused" appearance; extreme lethargy; staggering, stumbling, and being unable to walk without falling or losing their balance; drooling and vomiting; diarrhea (especially if a pet has consumed high-fat edibles, cannabutter, or oils); inability to control their bladders; abnormal heart rate and blood pressure; also called "Static Ataxia" or "Ataxia" in dogs.

34. Therapeutic Index - The term "therapeutic index" in this disclosure refers to the therapeutic window or safety window and comparison of the amount of a cannabinoid that causes the therapeutic effect to the amount that causes adverse effects.

35. Topical Formulation - For purposes of the present invention, a "topical formulation" includes, for example, ointments, creams, lotions, pastes, gels, etc., which releases one or more drugs (e.g., cannabinoid drug(s)s) at a predetermined rate over a defined period of time to a defined site of application.

36. Transdermal - For purposes of the present invention, "transdermal" delivery is the delivery by passage of a drug through the skin and into the bloodstream ("traditional" transdermal delivery) and is termed "transdermal systemic drug delivery (TSD) therapy).

37. Transdermal Therapeutic System - For purposes of the present invention, a "transdermal therapeutic system" is defined as a drug-containing device (including e.g., patch, disc, etc.) which releases one or more drugs at a predetermined rate over a defined period of time to a defined site of application.

38. Transmucosal – For the purposes of the present invention, "transmucosal" is a delivery method relating to, being, or supplying a medication that enters through or across a mucous membrane (as of the mouth).

39. Treating, Treatment, and Treat - As used herein, the terms "treating," "treatment," "treat" and the like mean affecting a subject (e.g. a patient), tissue or cell to obtain a desired pharmacological and/or physiological effect. The effect may be prophylactic in terms of completely or partially preventing, or reducing the severity of, a disease or associated symptom, and/or may be therapeutic in terms of a partial or complete cure of a disease. For example, a reference to "treating" inflammation may therefore encompass: (a) arresting the progress of the disease, e.g. preventing worsening of a symptom or complication over time; (b) relieving or ameliorating the effects of inflammation, i.e. causing an improvement of at least one symptom or complication of inflammation; (c) preventing additional symptoms or complications of inflammation from developing; and/or (d) preventing inflammation or a symptom associated with inflammation from occurring in a subject. In another example, a reference to "treating" pain may therefore encompass: (a) preventing the severity of the pain from increasing; (b) relieving or ameliorating the severity of pain as experienced by the subject; (c) preventing the spread of pain from its originating location; and/or (d) preventing or delaying the onset of pain in the subject. In a further example, a reference to "treating" anxiety may therefore encompass: (a) preventing the severity of the anxiety from increasing, for example by preventing increase of a subject's heart rate; (b) relieving or ameliorating the severity of the anxiety as experienced by the subject in the short and/or long term, for example by lowering a heart rate of a subject; (c) preventing additional symptoms associated with anxiety from developing; and/or (d) preventing or delaying the onset of anxiety in the subject.

40. Veterinary Acceptable - The term "veterinary acceptable" in the context of a form of a compound or an additive to the composition, is intended to mean that the form of the compound or the additive to the composition is suitable for use in a veterinary sense. Therefore, veterinary acceptable forms and/or additives are non-toxic to the non-human subject in the amounts in which they are present in the composition described herein.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A cannabinoid-terpenoid solution (CTS) for use in the administration of a cannabinoid-terpenoid medicament in a mammal, comprising:
    two or more cannabinoids;
    one or more terpenes; and
    wherein the one or more terpenes and two or more cannabinoids are mixed within the CTS to form a terpenoid to cannabinoid ratio with respect to one another that ranges from 1.2:1 to 4:1.

2. The cannabinoid-terpenoid solution as set forth in claim 1, wherein the two or more cannabinoids comprise at least two cannabinoids selected from a group consisting of cannabidiol (CBD), tetrahydrocannabinol (THC), cannabigerol (CBG), cannabinol (CBN), cannabichromene (CBC), cannabidivarin (CBDV), cannabidiolic acid (CBDA), tetrahydrocannabivarin (THCV), and tetrahydrocannabinolic acid (THCA).

3. The cannabinoid-terpenoid solution as set forth in claim 2, further comprising a lipophilic carrier mixed with the two or more cannabinoids and the one or more terpenes.

4. The cannabinoid-terpenoid solution as set forth in claim 3, wherein the two or more cannabinoids collectively comprise an amount less than or equal to 50 percent of the CTS, wherein the one or more terpenes comprise an amount less than or equal to 60 percent of the CTS, and wherein the lipophilic carrier comprises an amount less than or equal to 85 percent of the CTS.

5. The cannabinoid-terpenoid solution as set forth in claim 2, wherein the two or more cannabinoids comprise at least CBD and THC, and wherein the CBD comprises between 7 percent and 15 percent of the CTS and the THC comprises between 0.1 and 10 percent of the CTS, thereby forming a CBD dominant compound.

6. The cannabinoid-terpenoid solution as set forth in claim 5, wherein the CBD comprises between 10 percent and 14 percent of the CTS and the THC comprises between .3 percent and 1 percent of the CTS, thereby forming a CBD dominant compound.

7. The cannabinoid-terpenoid solution as set forth in claim 5, wherein the one or more terpenes comprise between 13 and 17 percent of the CTS.

8. The cannabinoid-terpenoid solution as set forth in claim 2, wherein the two or more cannabinoids comprise at least CBD and THC, and wherein the CBD comprises between 7 percent and 30 percent of the CTS and the THC comprises between 1 and 10 percent of the CTS, thereby forming a CBD rich compound.

9. The cannabinoid-terpenoid solution as set forth in claim 8, wherein the CBD comprises between 8 percent and 12 percent of the CTS and the THC comprises between 2 percent and 4 percent of the CTS, thereby forming a CBD rich compound.

10. The cannabinoid-terpenoid solution as set forth in claim 8, wherein the one or more terpenes comprise between 16 and 20 percent of the CTS.

11. The cannabinoid-terpenoid solution as set forth in claim 2, wherein the two or more cannabinoids comprise at least CBD and THC, and wherein the CBD comprises between 1 percent and 5 percent of the CTS and the THC comprises between 1 and 5 percent of the CTS, thereby forming a CBD:THC balanced compound.

12. The cannabinoid-terpenoid solution as set forth in claim 11, wherein the CBD comprises between 2 percent and 4 percent of the CTS and the THC comprises between 2 percent and 4 percent of the CTS, thereby forming a CBD:THC balanced compound.

13. The cannabinoid-terpenoid solution as set forth in claim 11, wherein the one or more terpenes comprise between 18 and 22 percent of the CTS.

14. The cannabinoid-terpenoid solution as set forth in claim 2, wherein the two or more cannabinoids comprise at least CBD and THC, and wherein the THC comprises between 7 percent and 30 percent of the CTS and the CBD comprises between 1 and 10 percent of the CTS, thereby forming a THC rich compound.

15. The cannabinoid-terpenoid solution as set forth in claim 14, wherein the THC comprises between 9 percent and 15 percent of the CTS and the CBD comprises between 2 percent and 4 percent of the CTS, thereby forming a THC rich compound.

16. The cannabinoid-terpenoid solution as set forth in claim 15, wherein the one or more terpenes comprise between 16 and 21 percent of the CTS.

17. The cannabinoid-terpenoid solution as set forth in claim 2, wherein the two or more cannabinoids comprise at least CBD and THC, and wherein the THC comprises between 7 percent and 15 percent of the CTS and the CBD comprises between 0.2 and 10 percent of the CTS, thereby forming a THC dominant compound.

18. The cannabinoid-terpenoid solution as set forth in claim 17, wherein the THC comprises between 10 percent and 14 percent of the CTS and the CBD comprises between 0.3 percent and 2 percent of the CTS, thereby forming a THC dominant compound.

19. The cannabinoid-terpenoid solution as set forth in claim 17, wherein the one or more terpenes comprise between 16 and 20 percent of the CTS.

20. The cannabinoid-terpenoid solution as set forth in claim 2, wherein the one or more terpenes is one or more terpenes selected from a group consisting of Beta-Caryophyllene, Linalool, D-Limonene, Beta-Myrcene, Alpha-Pinene, Humulene, and Guanine.

21. The cannabinoid-terpenoid solution as set forth in claim 20, wherein the one or more terpenes include one or more terpenes selected from a group consisting of Beta-Caryophyllene, Linalool, D-Limonene, Beta-Myrcene, Alpha-Pinene, Humulene, and Guanine to collectively form between 10 percent and 20 percent of the CTS.

22. The cannabinoid-terpenoid solution as set forth in claim 14, wherein the one or more terpenes collectively form between 12 percent and 18 percent of the CTS.

23. The cannabinoid-terpenoid solution as set forth in claim 3, wherein the lipophilic carrier is a medium chain triglyceride (MCT) oil.

24. The cannabinoid-terpenoid solution as set forth in claim 2, wherein at least one of the two or more cannabinoids is a highly purified extract of *cannabis* which comprises at least 90% Δ9-tetrahydrocannabinol (THC).

25. The cannabinoid-terpenoid solution as set forth in claim 2, wherein at least one of the two or more cannabinoids is a highly purified extract of *cannabis* which comprises at least 90% cannabidiol CBD.

26. The cannabinoid-terpenoid solution as set forth in claim 2, wherein at least one of the one or more terpenes is an extract selected from a group consisting of Beta-Carophyllene, Linalool, D-Limonene, Beta-Myrcene, Alpha-Pinene, Humulene, and Guanine.

27. The cannabinoid-terpenoid solution as set forth in claim 2, wherein at least one of the two or more cannabinoids is in a form selected from a group consisting of being derived from hemp and being synthetic.

28. The cannabinoid-terpenoid solution as set forth in claim 2, wherein the two or more cannabinoids include CBD and THC, such that the CTS comprises less than 0.3% THC.

29. The cannabinoid-terpenoid solution as set forth in claim 1, wherein the mammal selected from a group consisting of a canine, a feline, an equine, a bovine, a hircine, a porcine, a sheep, a lamb, a monkey, and an ape.

30. A cannabinoid-terpenoid solution (CTS) for use in the administration of a cannabinoid-terpenoid medicament in a mammal, comprising:
    two or more cannabinoids, the two or more cannabinoids comprising at least two cannabinoids selected from a group consisting of cannabidiol (CBD), tetrahydrocannabinol (THC), cannabigerol (CBG), cannabinol (CBN), cannabichromene (CBC), cannabidivarin (CBDV), cannabidiolic acid (CBDA), tetrahydrocannabivarin (THCV), and tetrahydrocannabinolic acid (THCA);
one or more terpenes mixed with the two or more cannabinoids to form the CTS; and
wherein the one or more terpenes and two or more cannabinoids are mixed within the CTS to form a terpenoid to cannabinoid ratio with respect to one another that ranges from approximately 1:2 to 4:1.

31. The cannabinoid-terpenoid solution as set forth in claim 30, wherein the two or more cannabinoids include at least CBD and THC, such that CBD and THC are mixed within the CTS to form a ratio with respect to one another, the ratio being selected from a group consisting of CBD dominant, CBD rich, CBD:THC balanced, THC rich, and THC dominant.

* * * * *